United States Patent [19]

Perron et al.

[11] Patent Number: 5,728,540
[45] Date of Patent: Mar. 17, 1998

[54] CYTOTOXIC FACTOR AS IS ASSOCIATED WITH MULTIPLE SCLEROSIS, ITS DETECTION AND ITS QUANTIFICATION

[75] Inventors: Hervé Perron, Grenoble; Tomas Dobransky, Marly-Le-Roy; François Rieger, Paris; Bernard Mandrand, Villeurbanne, all of France

[73] Assignee: Bio Merieux, Marcy L'etoile, France

[21] Appl. No.: 468,670

[22] Filed: Jun. 6, 1995

Related U.S. Application Data

[62] Division of Ser. No. 389,164, Feb. 15, 1995.

[30] Foreign Application Priority Data

Feb. 15, 1994 [FR] France ................................ 94 01946

[51] Int. Cl.$^6$ .............................. C12Q 1/37; C12Q 1/04; G01N 33/567; C12N 5/00
[52] U.S. Cl. ........................... 435/23; 435/34; 435/4; 435/18; 435/7.2; 435/7.21; 435/240.2; 435/240.1; 436/63; 436/74; 436/501; 436/171; 436/827; 436/828; 422/82.03; 422/55; 250/281; 356/302
[58] Field of Search ...................... 435/23, 34, 4, 435/18, 110, 106, 964, 7.2, 7.21, 240.2, 240.1; 424/9.2, 570, DIG. 16; 436/63, 74, 501, 512, 827, 171, 828; 530/903; 422/82.03, 55; 250/281; 356/302

[56] References Cited

U.S. PATENT DOCUMENTS

| | | |
|---|---|---|
| 4,311,686 | 1/1982 | Angers et al. |
| 4,346,074 | 8/1982 | Gilmour et al. |
| 4,388,298 | 6/1983 | Nazerian et al. |
| 4,396,600 | 8/1983 | Messineo et al. |
| 4,520,113 | 5/1985 | Gallo et al. |
| 4,647,773 | 3/1987 | Gallo et al. |
| 4,708,818 | 11/1987 | Montagnier et al. |
| 4,900,553 | 2/1990 | Silver et al. ..................... 435/23 |
| 5,158,976 | 10/1992 | Rosenburg et al. ................. 435/23 |
| 5,219,837 | 6/1993 | Cohen et al. ...................... 514/12 |
| 5,225,352 | 7/1993 | Zanetta et al. |
| 5,585,262 | 12/1996 | Perron et al. |

FOREIGN PATENT DOCUMENTS

| | | |
|---|---|---|
| 0 222 310 | 5/1987 | European Pat. Off. |
| 0 326 395 | 8/1989 | European Pat. Off. |
| 93/07259 | 4/1993 | WIPO |
| 93/20188 | 10/1993 | WIPO |
| WO 93/23550 | 11/1993 | WIPO |
| WO 94/28138 | 12/1994 | WIPO |

OTHER PUBLICATIONS

*ATCC Catalogue of Cell Lines and Hybridomas*, Sixth Edition, 1988, pp. 165 and 344–355.

C.R.M. Bangham et al., "PCR Analysis of DNA from Multiple Sclerosis Patients for the Presence of HTLV–1", *Science*, vol. 246, Nov. 10, 1989, pp. 821–824.

R. Baccala et al., "Genomically Imposed and Somatically Modified Human Thymocyte vb Gene Repertoires", *Proc. Natl. Acad. Sci.*, vol. 88, pp. 2908, 1991.

T. Bergström et al., "Isolation of Herpes Virus Type 1 During First Attack of Multiple Sclerosis.", *Annales Neurology*, vol. 26, pp. 283–285, (1989).

Bjare, "Serum–Free Cell Culture", *Pharmac. Ther.*, vol. 53, 1992, pp. 355–374.

C. Bosgiraud et al., "Ultrastructural Study on Visna Virus in Sheep Plexus Choroid Cells", *Biological Abstracts*, vol. 83, No. 7, 1987.

(List continued on next page.)

*Primary Examiner*—Louise Leary
*Attorney, Agent, or Firm*—Oliff & Berridge

[57] ABSTRACT

Gliotoxic factor in the isolated or purified state, characterized in that it possesses toxic activity with respect to human or animal astrocytic cells, having the effect of a cytomorphological disorganization of their network of intermediate filaments and/or a degradation of the proteins of said intermediate filaments and/or cell death, in particular by apoptosis.

20 Claims, 15 Drawing Sheets

OTHER PUBLICATIONS

D. Ross Boswell et al., "Sequence comparison and alignment: the measurement and interpretation of sequence similarity", *Computational Molecular Biology, Sources and Methods for Sequence Analysis*, pp. 161–178.

Chomczynski et al., "Single-Step Method of RNA Isolation by Acid Guanidinium Thiocyanate–Phenol–Chloroform Extraction", *Anal. Biochem.*, 1987, vol. 162, pp. 156–159.

Cook et al., "Multiple Sclerosis and Distemper in Iceland 1966–1978", *Acta Neurol. Scandinav.* 61, 1980, pp. 244–251.

S. Dhib–Jalbut et al., "Measles Virus Polypeptide–Specific Antibody Profile in Multiple Sclerosis", *Neurology*, vol. 40, pp. 430–435, (1990).

Dunn et al., "A Novel Method to Map Transcripts: Evidence for Homology Between and Adenovirus mRNA and Discrete Multiple Regions of the Viral Genome", *Cell*, vol. 12, Sep. 1977, pp. 23–36.

Elian et al., "Multiple Sclerosis Among United Kingdom–Born Children of Immigrants from the Indian Subcontinent, Africa and the West Indies", *J Neurol Neurosurg Psychiat*, 1990; 53, pp. 906–911.

E. J. Field, "Immunological Treatment for Multiple Sclerosis", *The Lancet*, Jun. 3, 1989, p. 1272.

Frohman et al., "Rapid Production of Full–Length cDNAs from Rare Transcripts: Amplification Using a Single Gene–Specific Oligonucleotide Primer", *Proc. Natl. Acad. Sci. USA*, 1988, vol. 85, pp. 8998–9002.

Medline Abstract of FU et al., "Rabies virus nucleoprotein expressed in and purified from insect cells is efficacious as a vaccine," Proc Natl Acad Sci USA 88: 2001–05 (1991).

M. B. Gardner et al., "Congenital Transmission of Murine Leukaemia Virus from Wild Mice Prone to Development of Lymphoma and Paralysis", *J. Natl. Cancer Inst.*, vol. 62, pp. 63–69, (1979).

M. B. Gardner, "Genetic resistance to a Retroviral Neurologic Disease in Wild Mice, in Retrovirus Infectious of the Nervous System", *Oldstone M.B.A. and Koprowsky H. Eds. Current Topice in Microbiology and Immunology*, No. 160, pp. 3–10, (Springer–Verlag, Berlin, 1990).

A. Gessain et al., "Intrathecal Synthesis of Antibodies to Human T Lymphotropic Virus Type I and the Presence of IgG Oligoclonal Bands in the Cerebrospinal Fluid of Patients with Endemic Tropical Spastic Paraparesis", *The Journal of Infectious Diseases*, vol. 157, No. 6, Jun. 1988, pp. 1226–1234.

A. Gessain et al., "Antibodies to Human T–Lymphotrophic Virus type–I in Patients with Tropical Spastic Paraparesis", *Lancet*, vol. 2, pp. 407–410, (1985).

F. Gonzalez–Scarano et al., "Sequence Similarities Between Human Immunodeficiency Virus gp41 and Paramyxovirus Fusion Proteins.", *AIDS Res. Hum. Retrov.*, vol. 3, pp. 245–252, (1987).

S.J. Greenberg et al., "Detection of sequences homologous to human retroviral DNA in multiple sclerosis by gene amplification", *Proc. Natl. Acad. Sci. USA*, vol. 86, Apr. 1989, pp. 2878–2882.

S. Haahr et al., "A Putative New Retrovirus Associated with Multiple Sclerosis and the Possible Involvement of Epstein–Barr Virus in this Disease", *NY Acad. Science*, vol. 724, pp. 148–156, 1994.

S. Haahr et al., "Is Multiple Sclerosis Caused by a Dual Infection with Retrovirus and Epstein–Barr Virus?", *Neuroepidemiology*, vol. 11, pp. 299–303, (1992).

S. Haahr et al., "Just Another Dubious Virus in Cells from a Patient with Multiple Sclerosis?", *The Lancet*, vol. 337, Apr. 6, 1991, pp. 863–864.

A. T. Haase, "Pathogenesis of Lentivirus Infections", *Nature*, vol. 322, Jul. 10, 1986, pp. 130–136.

S.L. Hauser et al., "Analysis of Human T–lymphotropic virus sequences in multiple sclerosis tissue", *Nature*, vol. 322, Jul. 10, 1986, pp. 176–178.

Hirayama et al., "Serum–Mediated Oligodendrocyte Cytotoxicity in Multiple Sclerosis Patients and Controls", *Neurology* 1986, vol. 36, pp. 276–278.

Hoffman et al., "Handbook of Clinical Neurology, 12; Viral Diseases", R.R. McKendall, ed., Elseveier Science Publishing, Amsterdam, 1989, pp. 453–466.

Huang, "Defective Interfering Viruses", *Fundamental Virology*, Fields et al., eds., 1986, pp. 101–117.

A. W. Hugin et al., "A Virus–Encoded Superantigen in a Retrovirus–Induced Immunodeficiency Syndrome of Mice", *Science*, vol. 252, pp. 424–427, (1991).

James, "Multiple Sclerosis or Blood–Brain Barrier Disease", *The Lancet*, Jan. 7, 1989, p. 46.

Medline abstract of Jarrett et al., "Studies on vaccination against papillomaviruses: a comparison of purified virus, tumour extract and transformed cells in prophylactic vaccination," Vet Rec 126: 449–52 (1990).

D. Johnson et al., "Quantitation of the Myelin–Associated Glycoprotein in Human Nervous Tissue from Controls and Multiple Sclerosis Patients", *Journal of Neurochemistry*, vol. 46, No. 4, 1986, pp. 1086–1093.

Johnson, "Viral Aspects of Multiple Sclerosis", *Handbook of Clinical Neurology*, vol. 3(47):Demyelinating Diseases, 1985, pp. 319–336.

R.T. Johnson, "Nononcogenic Retrovirus Infections as Models for Chronic and Relapsing Human Diseases: Introduction", *Reviews of Infectious Diseases*, vol. 7, No. 1, Jan.–Feb. 1985, pp. 66–67.

Karpas et al., "Lack of evidence for involvement of known human retroviruses in multiple sclerosis", *Nature*, vol. 322, 10 Jul. 1986, pp. 177–178.

H. Koprowski et al., "Multiple sclerosis and human T–cell lymphotropic retroviruses", *Nature*, vol. 318, Nov. 14, 1985, pp. 154–160.

G. La Mantia et al., "Identification of New Human Repetitive Sequences: Characterization of the Corresponding cDNAs and their Expression in Embryonal Carcinoma Cells", *Nucleic Acids Research*, vol. 17, No. 15, 5913–5922, (1989).

G. La Mantia et al., "Identification and Characterization of Novel Human Endogenous Retroviral Sequences Prefentially Expressed in Undifferentiated Embryonal Carcinoma Cells", *Nucleic Acids Res.*, 1991, vol. 19, No. 7, pp. 1513–1520.

H. Lassmann et al., "Chronic Relapsing Experimental Allergic Encephalomyelitis–Clinicopathological Comparison with Multiple Sclerosis", Arch Neurol, vol. 36, Aug. 1979, pp. 490–497.

Medline abstract of LEAO, "Tuberculosis: new strategies for the development of diagnostic tests and vaccines," Braz J Med Biol Res 26: 827–33 (1993).

Y.S. Lie et al., Journal of Virology, vol. 68, No. 12, Dec. 1994, pp. 7840–7849, "Chinese hamster ovary cells contain transcriptionally active full length type C provirises".

Linial et al., "Retroviral RNA Packaging: Sequence Requirements and Implications", in *Current Topics in Microbiology and Immunobiology. Retroviruses, Strategies of Replication*, Swanstrom et al., eds., vol. 157, 1990, pp. 125–152.

R. Lisak et al., "In Vitro Cell–Mediated Immunity of Cerebrospinal–Fluid Lymphocytes to Myelin Basic Protein in Primary Demyelinating Diseases", *The New England Journal of Medicine*, vol. 297, No. 16, Oct. 20, 1977, pp. 850–853.

Lori et al., "Viral DNA Carried by Human Immunodeficiency Virus Type 1 Virions", *J. Virol.*, vol. 66, No. 8, Aug. 1992, pp. 5067–5074.

F. Mallet et al., "Continuous RT–PCR and taq DNA Polymerase: Characterization and Comparison to Uncoupled Procedures", *Biotechniques*, vol. 18, pp. 678–687, 1985.

Mallet et al., "Enzyme–Linked Oligosorbent Assay for Detection of Polymerase Chain Reaction–Amplified Human Immunodeficiency Virus Type I", *J. Clin. Microbiol.*, Jun. 1993, vol. 31, No. 6, pp. 1444–1449.

P. Marrack et al., "A Maternally Inherited Superantigen Encoded by a Mammary Tumor Virus", *Nature*, vol. 349, pp. 524–526, (1991).

J. Merregaert et al., "Nucleotide Sequence of a Radiation Leukemia Virus Genome", *Virology*, vol. 158, No. 1, pp. 88–102, (1987).

Meyerhans et al., "Temporal Fluctuations in HIV Quasispecies in Vivo Are Not Reflected by Sequential HIV Isolations", *Cell*, vol. 58, Sep. 8, 1989, pp. 901–910.

J.D. Mosca et al., "Activation of human immunodeficiency virus by herpesvirus infection: Identification of a region within the long terminal repeat that responds to a trans–acting factor encoded by herpes simplex virus 1", *Proceedings of the National Academy of Sciences of USA*, vol. 84, No. 21, Nov. 1987, pp. 7408–7412.

O. Narayan et al., "Lentiviral Diseases of Sheep and Goats: Chronic Pneumonia Leukoencephalomyelitis, and Arthritis", *Reviews of Infectious Diseases*, vol. 7, No. 1, Jan.–Feb. 1985, pp. 89–98.

N. Nathanson et al., "Experimental Visna in Icelandic Sheep: The Prototype Lentiviral Infection", *Reviews of Infectious Diseases*, vol. 7, No. 1, Jan.–Feb. 1985, pp. 75–82.

Nielsen et al., "Sequence–Selective Recognition of DNA by Strand Displacement with a Thymine–Substituted Polyamide", *Science*, vol. 254, pp. 1497–1500, (1991).

Norby, "Viral Antibodies in Multiple Sclerosis", *Prog. Med. Virol.*, vol. 24 1978, pp. 1–39.

M. Ohta et al., "Sera from Patients with Multiple Sclerosis React with Human T Cell Lymphotropic Virus–I Gag Proteins but not Env Proteins—Western Blotting Analysis", The Journal of Immunology, vol. 137, No. 11, Dec. 1, 1986, pp. 3440–3443.

Medline abstract of Orlandi et al., "Characterization of the 175–kilodalton erythrocyte binding antigen of Plasmodium falciparum," Mol Biochem Parasitol 40: 285–94 (1990).

Ostrove et al., "Activation of the Human Innumodeficiency Virus by Herpes Simplex Virus Type 1", J Virol 61(12), Dec. 1987, pp. 3726–3732.

J.L. Pablos et al., "A novel retroviral POL sequence is present in patients with rheumatoid arthritis", & American College of Rheumatology 57th Annual Scientific Meeting, Nov. 7–11, 1993 San Antonio, Texas, USA, *Arthritis and Rheumatism*, vol. 36, No. 9 supl. 1993, p. S55, Abstract No. 102.

Medline abstract of PEI et al., "Identification, purification, and characterization of major antigenic proteins of Campylobacter jejuni," J Biol Chem 266: 16363–69 (1991).

H. Perron et al., "Leptomeningeal cell line from multiple sclerosis with rverse transcriptase activity and viral particles", Biological Abstracts, vol. 89, No. 9, May 1, 1990.

H. Perron et al., "Antibody to Reverse Transcriptase of Human Retrovirus in Multiple Sclerosis", Biological Abstracts, vol. 93, No. 6, Mar. 15, 1992.

H. Perron et al., "Herpes simplex virus ICPO and ICP4 immediate early proteins strongly enhance expression of a retrovirus harboured by a leptomeningeal cell line from a patient with multiple sclerosis", The Journal of General Virology, vol. 74, No. 1, Jan. 1993, pp. 65–72.

H. Perron et al., "Retrovirus Isolation from Patients with Multiple Sclerosis: Epiphenomenon or Causative Factor?", *AIDS Research and Human Retroviruses*, vol. 8, No. 5, May 1992, p. 922.

H. Perron et al., "In Vitro Transmission and Antigenicity of a Retrovirus Isolated from a Multiple Sclerosis Patient", *Res. Virol.*, vol. 143, No. 5, 1992, pp. 337–350.

Perron et al., "Retroviral Reactivation by Herpesviruses in MS: Serological Arguments", Current Concepts in Multiple Sclerosis 1991, pp. 331–332.

A. Plaza et al., "Theofilopoulos, A.N. New Human vβ 12DD Genes and Polymorphic Variants. J. Imm"; vol. 147, No. 12, pp. 4360–4365, 1991.

J. L. Portis, "Wild Mouse Retrovirus: Pathogenesis in Retrovirus Infections of the Nervous System". Oldstone M.B.A. and Koprowsky H. Eds. Current topics in microbiology and immunology, n°160, pp. 11–27, (Springer–Verlag, Berlin, 1990).

C.M. Poser et al., "New Diagnostic Criteria for Multiple Sclerosis: Guidelines for Research Protocols, in The diagnosis of Multiple Sclerosis", *Thieme Stratton Inc.*, pp. 225–229, 1984.

D.N., Posnet, "Do Superantigens Play a Role in Autoimmunity?", *Semin. Immunol.*, vol. 5, pp. 65–72, 1993.

E.P. Reddy et al., "Amplification and Molecular Cloning of HTLV–I Sequences from DNA of Multiple Sclerosis Patients", *Science*, vol. 243, Jan. 27, 1989, pp. 529–533.

S. S. Rhee et al., "A single Amino Acid Substitution within the Matrix Protein of a D–Type Retrovirus Converts Its Morphogenesis to that of a C–Type Retrovirus", Cell 63, pp. 77–86, (1990).

Riise et al., "Clustering of Residence of Multiple Sclerosis Patients at Age 13 to 20 Years in Hordaland, Norway", *Am J Epidemiol* 1991, vol. 133, No. 9, pp. 932–939.

Rosati et al., "Incidence of Multiple Sclerosis in the Town of Sassari, Sardinia, 1965 to 1985: Evidence for increasing Occurrence of the Disease", *Neurology* 38 (Mar. 1988), pp. 384–388.

Medline abstract of Rumschlag et al., "Immunologic characterization of a 35–kilodalton recombinant antigen of Mycobacterium tuberculosis," J Clin Microbiol 28: 591–95 (1990).

Medline abstract of Sakulramrung et al., "Antigenic and immunogenic characteristics of subcellular fractions and whole cells of a rough E. coli O111 (J5) mutant," Immunobiology 169: 372–88 (1985).

Shih et al., "Detection of Multiple, Novel Reverse Transcriptase Coding Sequences in Human Nucleic Acids: Relation to Primate Retroviruses", *J. Virol.*, Jan. 1989, vol. 63, No. 1, pp. 64–75.

M. Sommerlund et al., "Retrovirus–like particles in an Epstein–Barr virus–producing cell line derived from a patient with chronic progressive myelopathy", *Acta Neurol Scand*, 1993: 87: pp. 71–76.

P. Sonigo et al., "Nucleotide Sequence of Mason–Pfizer Monkey Virus: An immunosuppressive D–Type Retrovirus", Cell 45, pp. 375–385, (1986).

Southern, "Detection of Specific Sequences Among DNA Fragments Separated by Gel Electrophoresis", *J. Mol. Biol.*, 1975, vol. 98, pp. 503–517.

Suzumura et al., "Serum Cytotoxicity to Oligodendrocytes in Multiple Sclerosis and Controls: Assessment by $^{51}$Cr Release Assay", *J. Neuroimmunol.*, 11 (1986), pp. 137–147.

K.G. Warren et al., "Diagnostic Value of Cerebrospinal Fluid Anti–Myelin Basic Proteitn in Patients with Multiple Sclerosis", Annals of Neurology, vol. 20, No. 1, Jul. 1986, pp. 20–25.

D. L. Wilkinson et al., "Evidence for a functional subclass of the RTLV–H family of human endogenous retrovirus–like sequences", *J. Virol.*, vol. 67, pp. 2981–2989, (1993).

A. N. Davison et al., "Biosynthesis of Myelin and Neurotoxic Factors in the Serum of Multiple Sclerosis Patients", *Advances in Experimental Medicine and Biology*, vol. 100, pp. 19–25, 1978, month not available. please print.

D. Giulian et al., "Secretion of Neurotoxins by Mononuclear Phagocytes Infected with HIV–1", *Science*, vol. 250, Dec. 14, 1990, pp. 1593–1596. month not available. (please print).

H. Perron et al., "Isolation of Retrovirus from Patients with Multiple Sclerosis", *The Lancet*, vol. 337, Apr. 6, 1991, pp. 862–863. month not available. (please print).

Levi et al., "Human Immunodeficiency Coat Protein gp120 Inhibits the β–adrenergic Regulation of Astroglial and Microglial Functions", *Proc. Natl. Acad. Sci. USA*, vol. 90, Feb. 1993, pp. 1541–1545. month not available. (please print).

Bernton et al., "No Direct Neuronotoxicity by HIV–1 Virions or Culture Fluids from HIV–1 Infected T Cells or Monocytes", *Aids Research and Human Retroviruses*, vol. 8, No. 4, 1992, pp. 495–503. month not available.

Giulian et al., "The Envelope Glycoprotein of Human Immunodeficiency Virus Type 1 Stimulates Release of Neurotoxins from Monocytes", *Proc. Natl. Acad. Sci. USA*, vol. 90, 1993, pp. 2769–2773. month not available.

Prineas, "The Neuropathology of Multiple Sclerosis", *Handbook of Clinical Neurology*, vol. 3, (47), 1985, pp. 213–57. month not available.

Prineas et al., "Multiple Sclerosis: Remyelination of Nascent Lesions", *Annals of Neurology*, vol. 33, No. 2, Feb. 1993, pp. 137–151. month not available.

Boyle et al., "Cellular Immune Response in Multiple Sclerosis Plaques", *American Journal of Pathology*, vol. 137, No. 3, Sep. 1990, pp. 575–584. month not available.

Charcot, "Histolgie de la sclerose en plaques [Histology of Multiple Sclerosis]", Gaz. Hop. (Paris), 1868; 41, 554–66. month not available.

Hauw et al., "Aspects Anatomo–Pathologiques de la Sclerose en Plaques [Anatomopathological Aspects of Multiple Sclerosis]", La Sclerose en Plaques [*Multiple Sclerosis*], 9–47 (Rascol et al. eds., 1980). month not available.

Poirier et al., "La Barriere Hemato–Encephalique. Donnees Morphologiques [The Blood–Brain Barrier. Morphological Data]", *La Revue de Medecine Interne*, vol. IV, No. 2, Jun. 1983, pp. 131–144. month not available.

Gonzalez–Scarano et al., "Multiple Sclerosis Disease Activity Correlates with Gadolinium–Enhanced Magnetic Resonance Imaging", *Annals of Neurology*, vol. 21, No. 3 Mar. 1987, pp. 330–306. month not available.

Rapoport, *Blood–Brain Barrier in Physiology and Medicine*, 129 (1976). month not available.

Kent et al., "Cerebral Blood Flow, Cerebral Metabolism and Blood–Brain Barrier," *Handbook of Clinical Neurology*, vol. 56(12), 1989, pp. 79–91. month not available.

Prineas et al., "Macrophages, Lymphocytes, and Plasma Cells in the Perivascular Compartment in Chronic Multiple Sclerosis", *Laboratory Investigation*, vol. 38, No. 4, 1978, pp. 409–421. month not available.

Bergamini et al., "Multiple Sclerosis. I. The Immune Pathogenetic Hypothesis", *Riv. Neurol.*, vol. 59, No. 5, Oct. 1989, pp. 176–190. month not available.

Calder, et al., "MS: A Localized Immune Disease of the Central Nervous System", *Immunology Today*, vol. 10, No. 3, 1989, pp. 99–103. month not available.

Jervis et al., "Experimental Allergic Encephalomyelitis", *J. Neuropathol. Exp. Neurol.*, 1948; 7, pp. 309–20. month not available.

Prineas, "Pathology of the Early Lesion in Multiple Sclerosis", *Human Pathology*, vol. 6, No. 5, Sep. 1975, pp. 531–554. mont not available.

Escourolle et al., "Principales Donnees Morphologiques Approches Physiopathologiques et Etiologiques de la Sclerose en Plaques [Principal Morphological Data, Physiopathological and Etiological Approaches to Multiple Sclerosis]", *La Reveue du Praticien*, Paris, 1980; 30, pp. 2047–2053. month not available.

McDonald, "The Mystery of the Origin of Multiple Sclerosis", *J. Neurol. Neurosurg. Psych.*, 1986; 49, pp. 113–123. month not available.

Carp et al., "Viral Etiology of Multiple Sclerosis", *Prog. Med. Virol.*, vol. 24, pp. 158–177, 1978. month not available.

Marie, "Sclerose en Plaques et Maladies Infectieuses [Multiple Sclerosis and Infectious Diseases]", *Le Progres Medical*, 1884; 12, pp. 287–289. month not available.

Gay, "Is Multiple Sclerosis Caused by an Oral Spirochaete", *The Lancet*, Jul. 12, 1986, pp. 75–77. month not available.

De Keyser, "Autoimmunity in Multiple Sclerosis", *Neurology*, 38, Mar. 1988, pp. 371–374. month not available.

Juntunen et al. "Multiple Sclerosis and Occupational Exposure to Chemicals: A Co–Twin Study of a Nationwide Series of Twins", *Br. J. Int. Med.*, 1989; 46: pp. 417–419. month not available.

Ebers et al., "The Geography of MS Reflects Genetic Susceptibility", *Neurology*, 36, Apr. 1986, Suppl. 1, p. 108. month not available.

Haegert et al. "HLA–DRβ, –DQα, and –DQβ Restriction Fragment Length Polymorphisms in Multiple Sclerosis", *J. Neurosci. Res.*, 1989; 23, pp. 46–54. month not available.

Waksman, "Mechanisms in Multiple Sclerosis", *Nature*, vol. 318, Nov. 14, 1985, pp. 104–105. month not available.

Acha–Orbea et al., "Mis—A Retrovirus Exploits the Immune System", *Immunology Today*, vol. 12, No. 10, 1991, pp. 356–361. month nont available.

Cole et al., "The Mycoplasma Arthritidis T–Cell Mitogen, MAM: A Model Superantigen", *Immunology Today*, vol. 12, No. 8, 1991, pp. 271–276. month not available.

Rudge, "Does A Retrovirally Encoded Superantigen Cause Multiple Sclerosis?", *Journal of Neurology, Neurosurgery & Psychiatry*, 1991; 54, pp. 853–855. month not available.

Woodland, et al., "An Endogenous Retrovirus Mediating Deletion of αβ T cells?", *Nature*, vol. 349, Feb. 7, 1991, pp. 529–530. month not available.

Traugott, "Multiple Sclerosis: Relevance of Class I and Class II MHC–Expressing Cells to Lesion Development", *Journal of Neuroimmunology*, 16, 1987, pp. 283–302. month not available.

Williams et al., "Molecular Regulation of Apoptosis: Genetic Controls on Cell Death", *Cell*, vol. 74, Sep. 10, 1993, pp. 777–779. month not available.

Levine et al., "Conversion of Lytic to Persistent Alphavirus Infection by the bcl–2 Cellular Oncogene", *Nature*, vol. 361, Feb. 25, 1993, pp. 739–742. month not available.

Newell et al., "Ligation of Major Histocompatibility Complex Class II Molecules Mediates Apoptotic Cell Death in Resting B Lymphocytes", *Proc. Natl. Acad. Sci. USA*, vol. 90, Nov. 1993, pp. 10459–10463. month not available.

Selmaj, et al., "Tumor Necrosis Factor Mediates Myelin and Oligodendrocyte Damage In Vitro", *Annals of Neurology*, vol. 23, No. 4, Apr. 1988, pp. 339–346. month not available.

Barna et al., "Human Astrocytes Proliferate in Response to Tumor Necrosis Factor Alpha", *J. Neuroimmunol.*, 30 (1990), pp. 239–243. month not available.

Robbins et al., "Production of Cytotoxic Factor for Oligodendrocytes by Stimulated Astrocytes", *The Journal of Immunology*, vol. 139, No. 8, Oct. 15, 1987, pp. 2593–2597. month not available.

Beck et al., "Increased Production of Interferon Gamma and Tumor Necrosis Factor Precedes Clinical Manifestation in Multiple Sclerosis: Do Cytokines Trigger Off Exacerbations?", *Acta Neurol. Scand.*, 1988: 78, pp. 318–323. month not available.

Winfield et al., "Stress Proteins, Autoimmunity, and Autoimmune Disease", *Current Topics in Microbiology and Immunology*, vol. 167, Springer–Verlag, Berlin, 1991, pp. 161–189. month not available.

Brocke et al., "Induction of Relapsing Paralysis in Experimental Autoimmune Encephalomyelitis by Bacterial Superantigen", *Nature*, vol. 365, Oct. 14, 1993, pp. 642–644. month not available.

Ransohoff et al., "Heat–Shock Proteins and Autoimmunity: Implications for Multiple Sclerosis", *Annals of Neurology*, vol. 34, No. 1, Jul. 1993, pp. 5–7. month not available.

Perron et al., "Leptomeningeal Cell Line from Multiple Sclerosis with Reverse Transcriptase Activity and Viral Particles", *Res. Virol.*, 1989, 140, pp. 551–161. month not available.

Perron et al., "Isolations of an Unknown Retrovirus from CSF, Blood and Brain Cells of Patients with Multiple Sclerosis", *Current Concepts in Multiple Sclerosis*, 1991, Elsevier, Amsterdam, pp. 111–116. month not available.

Dalgleish et al., "Do Human T–Lymphotrophic Viruses (HTLVs) and Other Enveloped Viruses Induce Autoimmunity in Multiple Sclerosis?", *Neuropath. App. Neurobiol.*, 1987, 13, pp. 241–250. month not available.

Birnbaum et al., "Spinal Fluid Lymphocytes from a Sub–Group of Multiple Sclerosis Patients Respond to Mycobacterial Antigens", *Ann. Neurol.*, vol. 34, No. 1, Jul. 1993, pp. 18–24. month not available.

Galiana et al., "Establishment of Permanent Astroglial Cell Lines, Able to Differentiate in Vitro, From Transgenic Mice Carrying the Polyoma Virus Large T Gene: An Alternative Approach to Brain Cell Immortalization", *Journal of Neuroscience Research*, 1990; 26: pp. 269–277. month not available.

Mosmann, "Rapid Colorimetric Assay for Cellular Growth and Survival: Application to Proliferation and Cytotoxicity Assays", *Journal of Immunological Methods*, 65, 1983, pp. 55–63. month not available.

Wollinsky et al., "Liquorpherese bei 10 Patienten mit Multipler Sklerose [Fluid Pheresis in 10 Patients With Multiple Sclerosis]", Verhandlungen der Deutschen Gesellschaft fur Neurologie, vol. 7, 1992, pp. 444–445. month not available.

Bradford, "A Rapid and Sensitive Method for the Quantitation of Microgram Quantities of Protein Utilizing the Principle of Protein–Dye Binding", *Anal. Biochem.*, 72, 1976, pp. 248–254. month not available.

Silberberg et al., "Tissue Culture Demyelination by Normal Human Serum", *Annals of Neurology*, vol. 15, No. 6, Jun. 1994, pp. 575–580. month not available.

Lo et al., "Newly Discovered Mycoplasma Isolated from Patients Infected with HIV", *The Lancet*, vol. 338, Dec. 7, 1991, pp. 1415–1418. month not available.

Huck et al, "J. Neurosci," vol. 4, No. 10, pp. 2650–2657, 1984. month not available. (please print).

Asai et al, "J. Neurochem", vol. 59, No. 1, pp. 307–317, 1992. month not available. (please print).

Webster's 9th New Collegiate Dictionary, p. 863, 1990. month not available. (please print).

Prineas, John W., "Handbook of Clin Neurology", vol. 3(47), 1985, pp. 213–257. month not available. (please print).

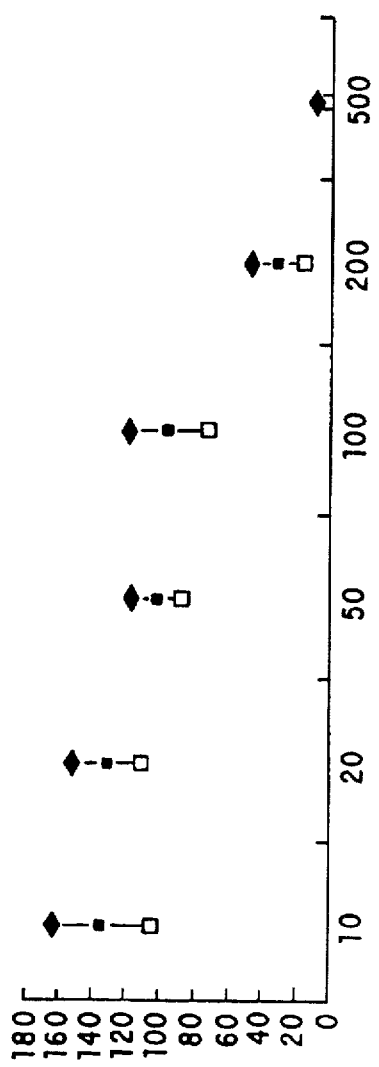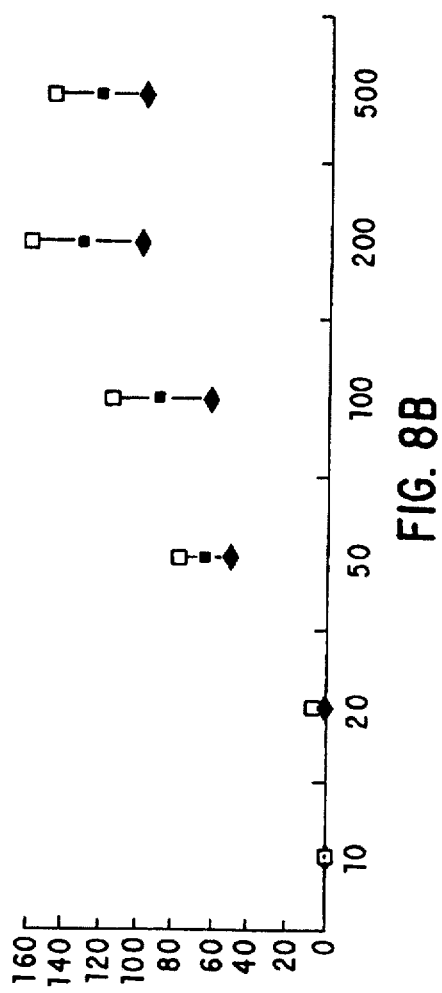
FIG. 8A
FIG. 8B

CYTOTOXIC FACTOR AS IS ASSOCIATED WITH MULTIPLE SCLEROSIS, ITS DETECTION AND ITS QUANTIFICATION

This is a division of copending application Ser. No. 08/389,164 filed Feb. 15, 1995.

FIELD OF THE INVENTION

The present invention relates to a cytotoxic factor associated with multiple sclerosis, characterized by its cytotoxic activity with respect to glial cells, in particular astrocytes, as well as to the demonstration of this cytotoxic activity in a biological test of detection and of monitoring this disease in biological fluids of patients suffering, in particular, from multiple sclerosis.

BACKGROUND

Glial cells (astrocytes, oligodendrocytes, microgliocytes) are the primary or secondary target of pathological processes in various diseases of the nervous system, in particular, in man, in leukoencephalitis, leukodystrophies, some forms of encephalopathy, some neurodegenerative diseases such as amyotrophic lateral sclerosis where there is a concomitant astrocytic gliosis with neuronal involvement, and lastly inflammatory diseases such as multiple sclerosis or Schilder's disease.

Multiple sclerosis (MS) is a chronic disease of the central nervous system in man, developing in a succession of phases of remission and exacerbation or according to a steady progression, and the anatomopathological feature of which consists of the formation of well-delimited patches of demyelination in the white matter of the brain and spinal cord (1). At histological level, these patches display, at the early stage of the lesion process, a degradation of the periaxonal myelin associated with an involvement of the glial cells responsible for this myelination, the oligodendrocytes (2). An inflammatory macrophage activation involving microglial cells (tissue macrophages resident in the central nervous system) as well as, probably, macrophages originating from infiltrated blood monocytes, is associated with this demyelination process and contributes to the destruction of the myelinated layers (3). In the center of the demyelinated patch, a relative depletion of glial cells is to be found, whereas a proliferation of astrocytes, or astrocytic gliosis, develops at the periphery and can, at a later stage, invade the demyelinated plaque to generate a fibrous or gliotic plaque, as is found on the site of old lesions (1). These sclerotic structures are the origin of the name given to the disease, multiple "sclerosis" (4).

Another feature of these plaques is their almost invariable association with a vascular element around which they appear to develop (5, 1). At histological level an adverse change in the blood-brain barrier (BBB) consisting of capillary endothelium is commonly observed in them (6). In effect, the vascular endothelium of capillary structures is normally butt-jointed in the central nervous system, except for the fenestrated capillaries associated with the choroid plexus, periventricular structures providing for the production of cerebrospinal fluid (7). This change in the BBB, marked by a parting of the endothelial cells and by the uncontrolled passage of a flow of plasmatic fluid and of cells of blood origin into the neuroglial parenchyma, may be visualized in "active" plaques by the magnetic resonance imaging (MRI) technique combined with the intravenous injection, into the patient under examination, of a solution of gadolinium. This compound enables a contrasted magnetic resonance signal to be obtained in the plasmatic fluid, and makes it possible to detect the abnormal passage of plasma into the nervous parenchyma with the edema resulting therefrom. It has been possible to show a correlation between the lesion-inducing activity of the plaques and the presence of this edema at the same level, as well as between the appearance and resorption of this edema and the regression of clinical exacerbations of the disease (8).

One of the decisive factors in maintaining a butt-jointed structure of the cerebral capillary endothelium, and hence in the endothelium of the BBB, consists of the underlying presence of cytoplasmic processes in the astrocytes, known as astrocyte feet (6). Probably, these astrocyte feet induce the formation or permit the maintenance of leakproof junction structures (of the zonula occludens type) which provide for the cohesion of the capillary endothelium barrier which is the material expression of the BBB. Now, various pathological models report the adverse change in the BBB associated with a depletion of astrocyte feet (9, 10).

Moreover, in the lesion process of MS, the adverse change in the BBB contributes to an amplification of the associated inflammatory response, through the afflux, rendered "free", of lymphoid cells originating from the blood circulation (11).

The contribution of the inflammation associated with immune cells is considerable in MS and participates in the lesion process, in particular via lymphocytes and self-reacting antibodies (12, 13). However, contrary to the autoimmune animal model of experimental allergic encephalitis, where the involvement of the BBB and the invasion of the nervous parenchyma by lymphoid cells of the circulating blood initiate the neuroglial lesion process (14), it is observed in MS that early lesion processes associated with a local macrophage reaction in the nervous parenchyma seem to precede the invasion of the tissue by lymphoid cells of the circulating blood (15, 3). It is thus apparent that lymphoid cells, and more especially lymphocytes, are not the prerogative of recent plaques (16). Furthermore, the density of the lymphocytic infiltration is most especially pronounced in the perivascular areas and at the periphery of the active plaques of demyelination (11, 3).

The initial stimulus at the origin of MS is at the heart of the debate about the etiology of MS (17). Arguments have been put forward, in turn, in favor of a viral (18), bacterial (19, 20), autoimmune (21, 13), toxic (22) or genetic (23, 24) hypothesis. In fact, it appears that a combination of a genetic predisposition to the action of a primary pathogenic agent may lead up to a devastating inflammatory and autoimmune process (25).

Different sequences of events may thus explain the demyelination and the functional neurological involvement in MS, without it having been possible to date to identify a decisive factor which might initiate and give a coherent explanation to the multitude of fragmented data which have accumulated concerning this disease.

Some molecules of bacterial or viral, or even endogenous retroviral, origin are known to possess so-called superantigenic properties (26, 27). Their particular properties of direct stimulation of T lymphocytes, specific to different antigens, by binding to the $V\beta$ region of certain "T" receptors, have suggested the hypothesis that such molecules are intimately associated with the etiopathogenic process of MS (28). Now, one of the characteristic effects of these superantigens on T cells is the premature induction, under certain conditions, of a programmed cell death or apoptosis (29). Superantigens also have properties of binding to HLA class II molecules at the surface of cells presenting the antigen (27). It may thus be recalled that astrocytes possess the capacity to express HLA class II antigens at their plasma membrane, and in particular in response to certain pro-inflammatory cytokines such as gamma interferon or tumor necrosis factor alpha (TNF-alpha) (30). However, no superantigen has yet been demonstrated in multiple sclerosis.

Moreover, many "untimely" apoptotic processes, as opposed to the normal apoptotic processes linked, for example, to the development of the nervous system (31), may take place in the absence of superantigen, either in the context of viral infection (32) or in the context of stimulation of a cell receptor (33). It is also of interest to note that an apoptosis may be induced by the in vitro stimulation of a TNF-alpha membrane receptor (31), but such a phenomenon has not been studied in the nervous system, and a fortiori with astrocytes.

Some cytokines may hence trigger a pathogenic process and be produced, in particular by macrophages, and they have a cytotoxic effect on oligodendrocytes (34). It should be noted that TNF-alpha, as well as interleukin-1-alpha, interleukin-1-beta, interleukin-2, interleukin-6 and gamma interferon, do not in principle have a cytolytic effect on astrocytes, but induce, rather, an astrocyte proliferation (35). However, astrocytes can themselves be subjected to stimulations at the origin of a secretion of TNF-alpha. This may be observed, for example, in response to lipopolysaccharide bacterial toxins or to calcium ionophores (36). Thus, an involvement of the oligodendrocytes, and hence a destruction of the myelin layers, may take place indirectly via the TNF-alpha produced by astrocytes. Any molecule which induces such a cytokine production by astrocytes, irrespective of its specific effect on the latter (proliferation, differentiation or cytopathogenic effect) is hence potentially demyelinating. TNF-alpha induces an oligodendrocytic cytotoxic mechanism whose primary effects are marked by a swelling of the myelin structures, suggestive of an ion channel-mediated action (34). A correlation seems, moreover, to exist between the production of TNF-alpha in vivo and exacerbations of MS (37). The role of astrocytes in such a production of TNF-alpha in patients suffering from MS is, however, unknown.

At all events, since astrocytes are capable of producing TNF-alpha and of copresenting a target antigen with HLA class II antigens to immunocompetent cells, which are themselves recruited by a cytopathic and/or inflammatory process, they are, in fact, at the pivotal point of the immunopathological interactions such as may be observed in the demyelinating lesion process which characterizes MS.

Another type of molecule capable of playing a part in the pathogenic process leading to the formation of a demyelination plaque, and then to an astrocytic gliosis, consists of the so-called heat shock proteins (HSP) or stress proteins. These proteins constitute a relatively conserved phylogenetic family and are to be found both in prokaryotes and in higher vertebrates (38). Their synthesis is inducible in eukaryotic cells by various stresses, in particular infectious or thermal stresses, and their interspecies antigenic likeness has suggested a possible induction of autoimmunity in man by infectious bacteria carrying HSP, such as Mycobacterium tuberculosis (39).

Bacterial antigens capable of possessing superantigenic properties or of being heat shock proteins have been implicated in the induction of exacerbations of MS, without it being clearly established to date whether they are chance cofactors of pathogenicity or are etiological agents, or are alternatively pathogens sharing common properties responsible for an identical pathogenicity (40, 42).

This type of mechanism involves, on the one hand, the presence of exogenous HSP (for example bacterial HSP) against which the immunocompetent cells become sensitized, and on the other hand the expression of endogenous HSP (of the infected body) at the surface of cells expressing HLA class II antigens. If the cellular HSP share common epitopes with the exogenous HSP, they may be recognized as "infectious" by sensitized lymphocytes. Their role has also been mentioned in MS (42). The "gliotoxicity" of such molecules may proceed via the immune response and, possibly, via the astrocytic cells or the microgliocytes (other macrophage glial cells capable of presenting a specific antigen), but the distinctive cytopathic effects of some HSP on glial cells are unknown in view of the absence of exhaustive studies in this field.

Some investigations carried out have provided arguments in favor of a viral etiology of MS (in particular 43, 44, 45 and WO-93/20188 (1993), the content of which is incorporated byway of reference).

Following the abovementioned investigations, the present inventors were led to look for one or more factors which are effectors of the pathogenic process ending in the typical formation of demyelination plaques and in an astrocytic gliosis.

Although cultures of multiple sclerosis blood monocytes/macrophages contributed to supporting a viral hypothesis during the abovementioned investigations, other aspects of the role of macrophage cells in the pathogenesis of this disease, which do not necessarily involve a viral agent, must be taken into consideration; in this connection, a hypothesis has hence been put forward and verified, according to which one or more factor(s) which is/are toxic to macroglial cells (astrocytes, oligodendrocytes) might be produced by the monocites of patients suffering from MS.

Although the molecular factors in question are unknown, a toxic factor originating either from immune or inflammatory cells or from a viral or bacterial agent, or alternatively induced by these latter in the surrounding cells, is capable of initiating a process ending in an acute or chronic inflammatory response.

The double uncertainty about the possible retroviral origin of MS (46) and about the possible contribution of a bacterial agent to its pathogenesis (40, 47) confirms the investigators in their search for factors which are cytotoxic to macroglial cells in patients suffering from MS. In effect, the glial cells are the ones which constitute the main target of the neuropathological process in MS.

A. N. Davison et al. (48) have studied the activity of oligodendrocytes, which are the cells involved in myelin synthesis, and in particular the factors capable of participating as a myelin synthesis inhibitor. These investigations are, however, exclusively limited to oligodendrocytes, and do not enable progress to be made in explaining the pathogenic process described above.

SUMMARY OF THE INVENTION

Thus, the subject of the invention is a gliotoxic factor, in the isolated or purified state, which possesses toxic activity with respect to human or animal astrocytic cells, said activity having the effect of a cytomorphological disorganization of their network of intermediate filaments and/or a degradation of the proteins of said intermediate filaments and/or cell death, in particular by apoptosis.

Gliotoxic factor is understood to mean a particular molecule, or a factor represented by a set of molecules capable of being defined, displaying biological activity which can be demonstrated by a cytotoxic effect on glial cells.

The inventors were able to demonstrate that the toxic activity of the abovementioned factor was associated with at least one globular glycoprotein.

According to the invention, glycoprotein is understood to mean a protein with which at least one carbohydrate group is combined by covalent bonding.

In addition, they characterized a gliotoxic factor which proves, according to the invention, after successive treatment on an ion exchange resin and then on a column for separation by exclusion, to consist preponderantly of a light fraction centered around an apparent molecular weight of approximately 17 KD, and of a less abundant heavy fraction centered around an apparent molecular weight of approximately 21 KD, at least said light fraction being resistant, under nondenaturing conditions, to the hydrolytic action of pronase, trypsin or proteinase K, and each of the two said fractions displaying a strong affinity for lectins and in particular concanavalin A.

The gliotoxic factor according to the invention has a major use in the diagnosis, but also in the prophylaxis and the therapy of MS.

According to the invention, a gliotoxic factor is capable of being obtained using the method comprising the following steps:

the starting material is a biological sample taken, for example, from a patient suffering from clinically active multiple sclerosis, said sample is treated successively on an ion exchange resin and then on a column for separation by exclusion, to obtain a gliotoxic factor consisting preponderantly of a light fraction centered around an apparent molecular weight of approximately 17 KD, and a less abundant heavy fraction centered around an apparent molecular weight of approximately 21 KD, each of said fractions possessing gliotoxic activity and having, in addition, the resistance and/or affinity properties mentioned above.

Biological sample according to the invention is understood to mean, in particular, a sample of the fluid, tissue or tissue fragment, mucosa, organ or organ fragment type, or culture supernatant obtained using one of the abovementioned samples.

Another subject of the invention is a method for detecting and/or monitoring the activity and/or predicting a pathology such as multiple sclerosis, consisting in detecting, in a biological sample, the presence and/or the amount of a gliotoxic factor as is defined by the invention.

Preferably, the biological sample containing the gliotoxic factor undergoes a pretreatment process, characterized in that, in order to remove contaminants liable to produce the spurious and nonspecific cytotoxic activity of the gliotoxic factor of the invention, a treatment of said sample with at least one of the following treatments is performed:

said sample is brought into contact with protein A, said sample is brought into contact with an ion exchange resin, said sample is brought into contact with a lectin and in particular concanavalin A.

The present invention also relates to a method for detecting and/or quantifying, in a biological sample, the toxic activity of the gliotoxic factor described above, consisting in incubating said biological sample in a suitable culture medium containing astrocytes, in particular immortalized astrocytes, enabling them to be cultured, and in detecting and/or quantifying the dead astrocytes and/or the living astrocytes.

To detect and/or quantify the dead astrocytes and/or the living astrocytes, different assay techniques may be employed, and especially the following:

a colorimetric assay employing calcein-AM and ethidium homodimer, respectively, a colorimetric assay employing methyltetrazoliumbromide a radioactive assay employing $^{51}Cr$.

According to the invention, another method for detecting and/or quantifying, in a biological sample, the toxic activity of a gliotoxic factor comprises a step of incubation of said sample in a suitable culture medium containing astrocytes, in particular immortalized astrocytes, enabling them to be cultured, and a step of detection and/or quantification of the fragmentation of the DNA of the astrocytes and/or of the cytomorphological disorganization of the network of intermediate filaments and/or of the degradation of the proteins of said intermediate filaments.

In a method of the invention for detecting, in a biological sample, the presence of a gliotoxic factor, the properties of the latter are utilized by carrying out a step of capture of said factor by a lectin and in particular concanavalin A, and/or a detection step based on the affinity of said factor for a said lectin.

Lastly, the final subjects of the invention are diagnostic and/or therapeutic and/or prophylactic compositions comprising all or part of a gliotoxic factor of the invention, natural or synthetic or obtained by genetic engineering, and/or a ligand specific to said factor.

More generally, the present invention may be applied to a device for carrying out a biological test using, for example, an ELISA technique, possessing a support or a substrate capable of binding to the factor of the invention.

Throughout the text, examples, tables and attached figures, when the diagnosis of MS is mentioned, it is understood to be a diagnosis of definite MS defined by the criteria of Poser (49).

BRIEF DESCRIPTION OF THE DRAWINGS

A better understanding of the invention will be gained on reading the detailed description which follows, given with reference to the attached figures, wherein:

FIG. 8 illustrates the mean number of dead (FIG. 8A) or living (FIG. 8B) astrocytic cells after mixing with a monocyte/macrophage culture supernatant at different dilutions. The means of the counts of the dead and living cells as a function of the dilution of the gliotoxic sample are represented by black squares on two separate graphs. The confidence intervals corresponding to each mean are represented by an upper value and a lower value separated by two standard deviations.

Figure 10A:
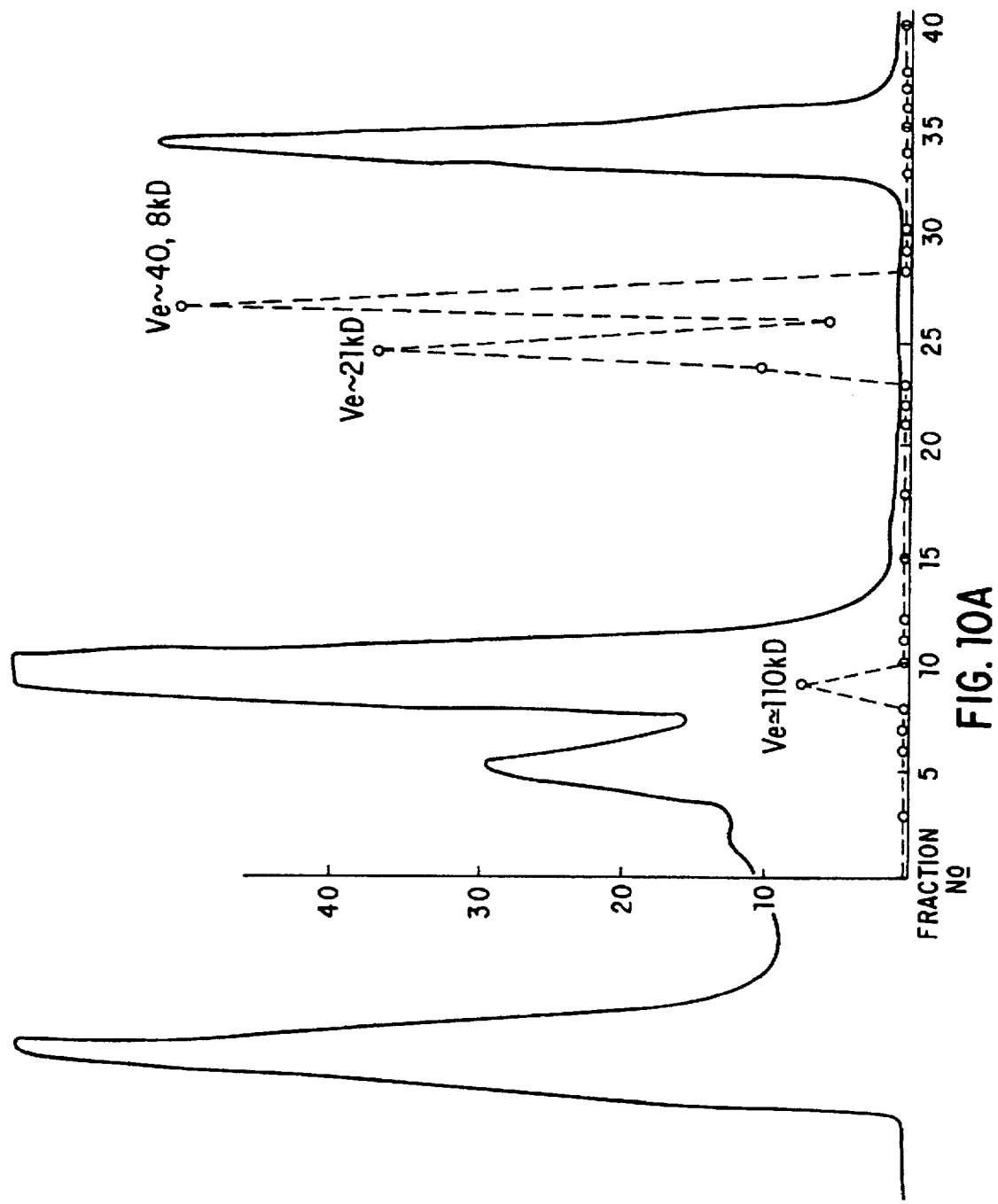
FIGS. 10A and 10B show the elution, in 50 mM Tris-HCl buffer, pH 6.8 on a Superose 12 exclusion column, of a gliotoxic fraction obtained after passage through DEAE-Sepharose resin and originating from a mixture of MS monocyte/macrophage culture supernatants sampled at $D_6$, $D_9$, D12 and $D_{16}$ according to FIG. 10A and sampled at $D_6$, $D_9$, $D_{13}$ and $D_{16}$ according to FIG. 10B; the thick line shows the absorption of the protein components at 280 nm with a coefficient of sensitivity of R=1.2; the broken line shows the gliotoxic activity measured on successive fractions according to the protocol described later in the description. The apparent molecular weights corresponding to the elution volumes (Ve) of the gliotoxicity peaks appear at the top of these peaks.
Figure 10B:
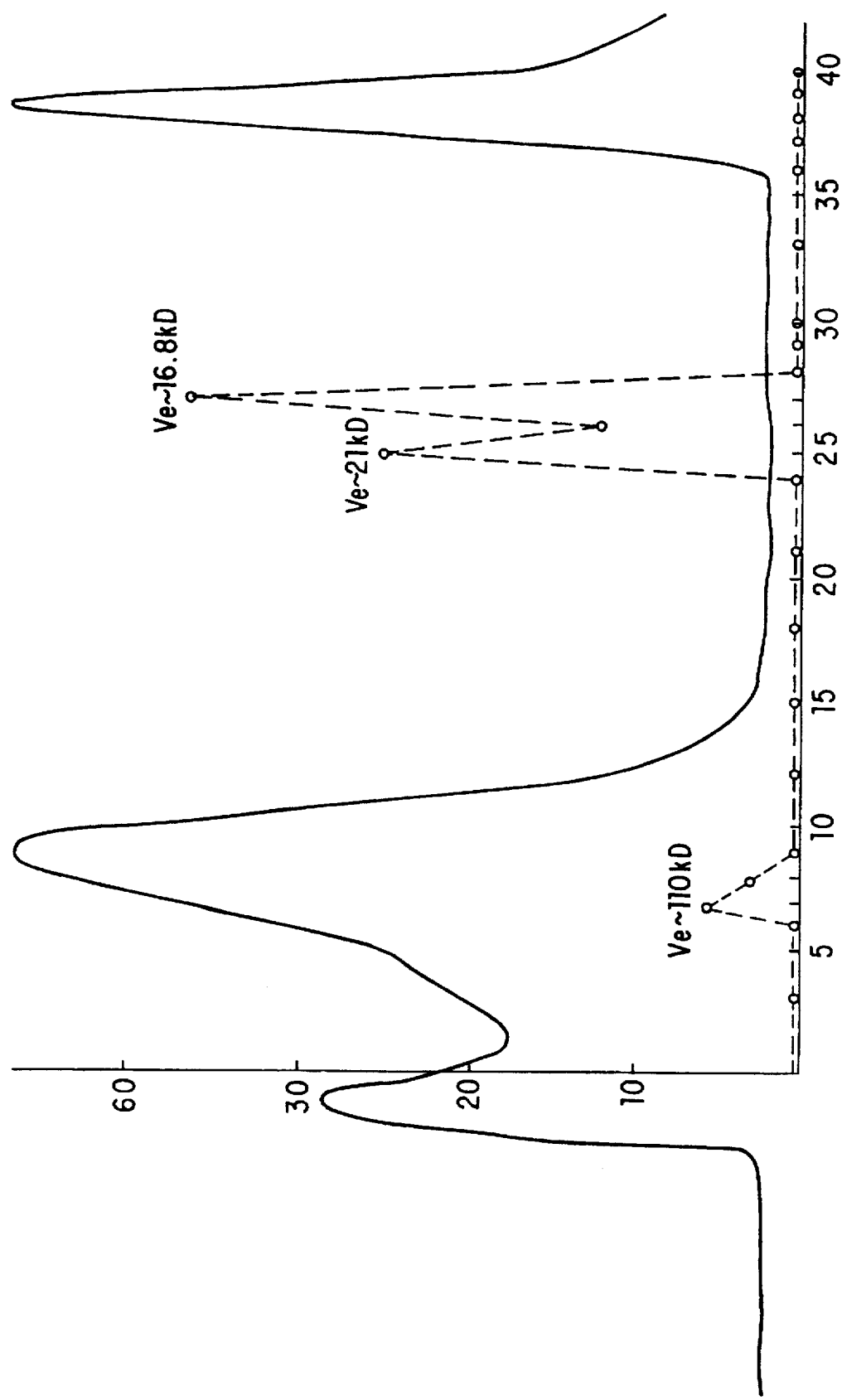

According to FIG. 10A, elution is done in the absence of urea, and according to FIG. 10B, elution is done in the presence of 8M urea.

Figure 11:
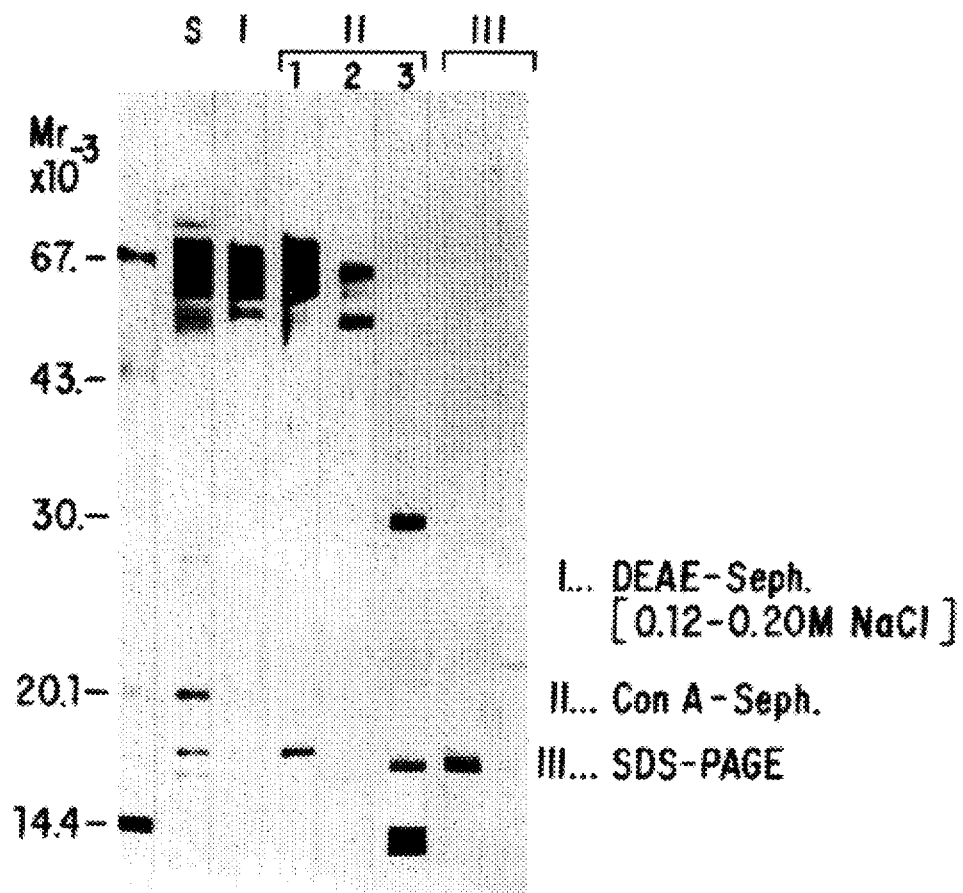

FIG. 11 illustrates a one-dimensional SDS-polyacrylamide electrophoresis gel showing, in successive wells, the implementation of a protein purification of the gliotoxic factor, starting from a crude MS monocyte/ macrophage culture supernatant and ending, after passage through a DEAE and then concanavalin A column, with the isolation of protein bands of 17 and 21 KD bearing virtually the whole of the activity of the sample.

Figure 12:
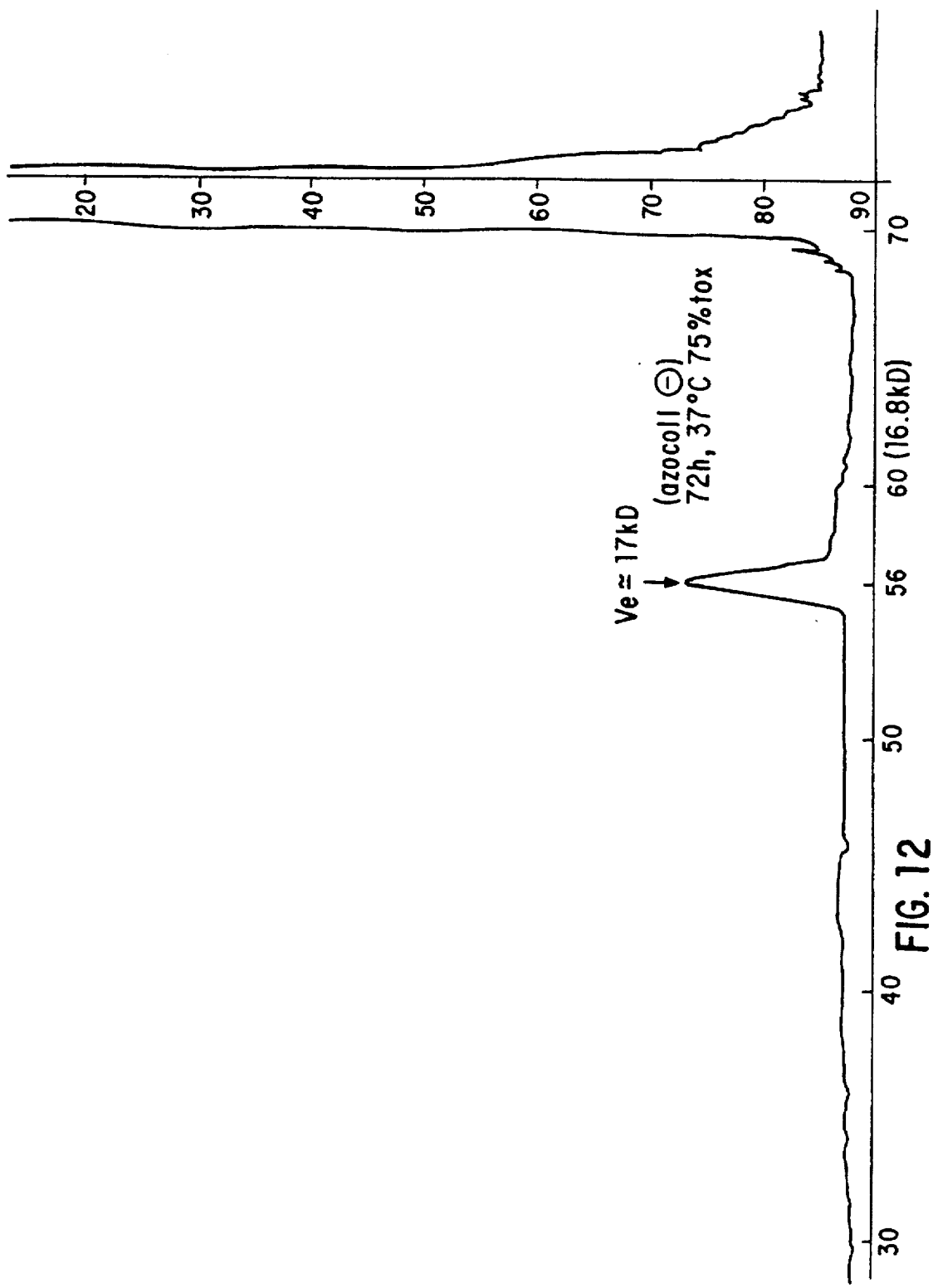
Figure 13:
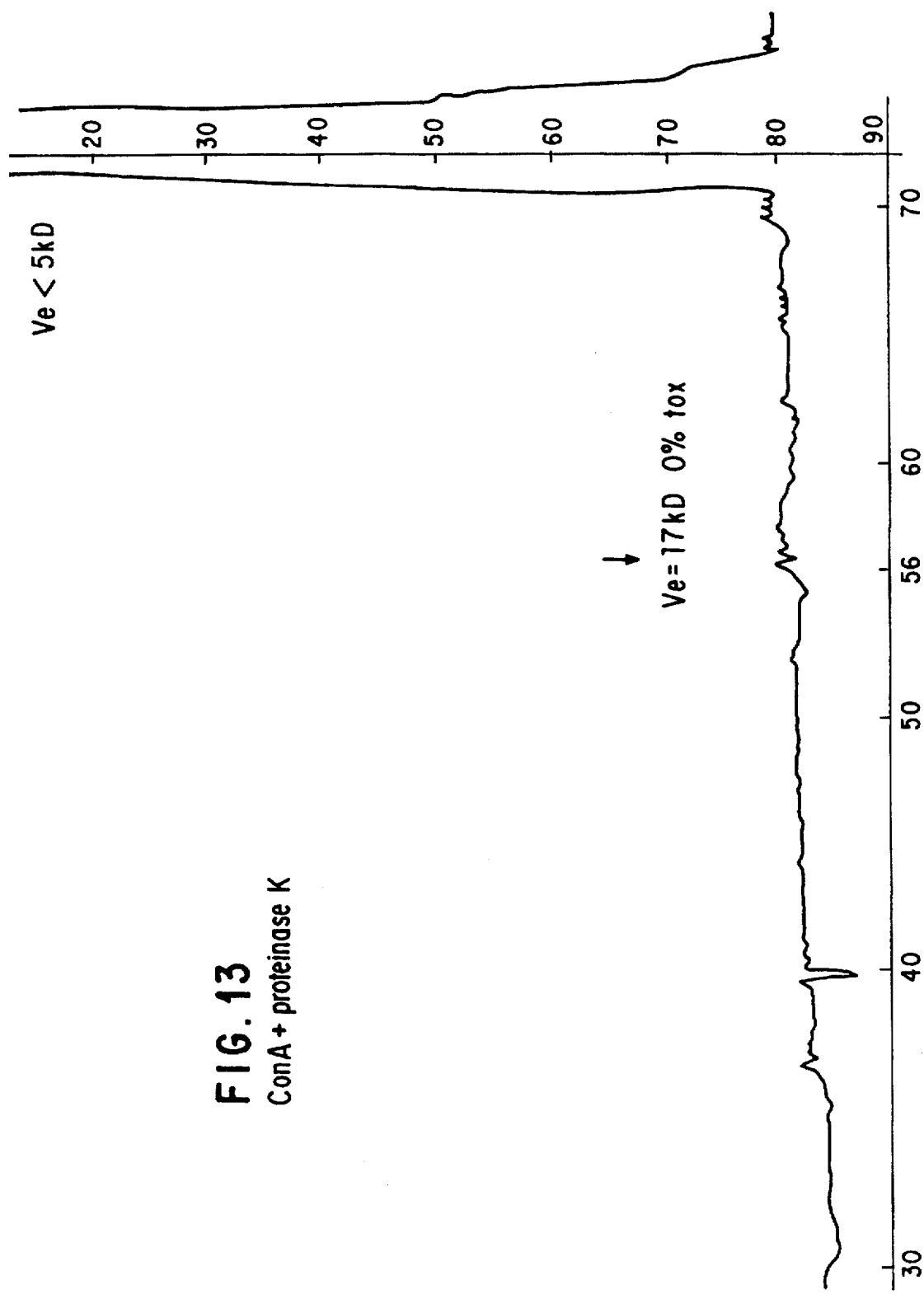

FIGS. 12 and 13 illustrate the elutions, on a Superose 12 column in a buffer containing 50 nM Tris-HCl, pH 6.8 with 8M urea, of fractions previously obtained in the eluate in pH 3 glycine buffer from a Con A-Sepharose column. These eluates were incubated in the presence of proteinase K before passage through Superose 12.

FIG. 12 shows a fraction originating from an MS gliotoxic culture supernatant or monocytes, and FIG. 13 shows a fraction originating from a nongliotoxic control culture supernatant.

The curve shows, in each case, the absorption at 280 nm of the peptide components with a sensitivity of detection R=0.02.

The level of elution of 17-KD standard protein is indicated by an arrow.

Figure 14:
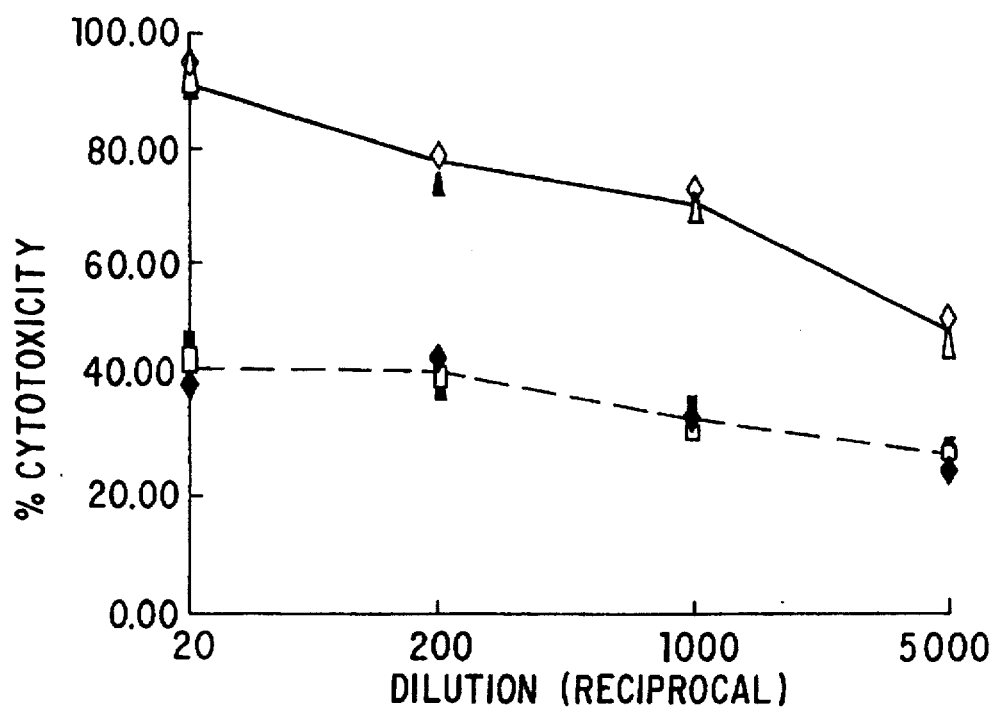

FIG. 14 shows the dose-response effect in a $^{51}Cr$ cytotoxicity test after 72 h of incubation, the dotted curve corresponding to the values obtained for an MS monocyte culture supernatant, and the curve in a continuous line corresponding to the values obtained for a fraction purified on Con A originating from the same culture supernatant.

Figure 15:
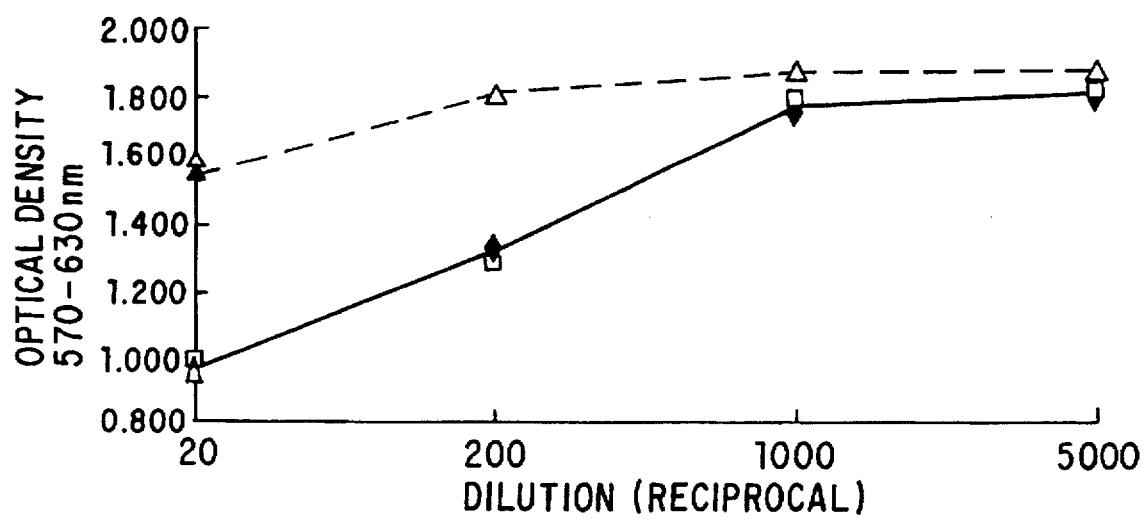

FIG. 15 shows the dose-response effect in a methyltetrazolium cytotoxicity test after 72 h of incubation, the dotted curve corresponding to the values obtained, in three measurements, for an MS monocyte culture supernatant, and the curve in a continuous line corresponding to the values obtained for a fraction purified on Con A originating from the same culture supernatant.

EXAMPLES

The first investigations employed, as biological fluids to be analyzed, the in vitro culture supernatants of monocytes/ macrophages from patients suffering from MS or from healthy controls or those suffering from other neurological diseases and, as substrate for detection of a cytotoxic effect, in vitro cultures of explants of rat embryonic cerebral cortex.

Example 1

Culturing of Blood Monocytes/Macrophages

The culture medium comprises RPMI1640 (Boehringer), penicillin-streptomycin (bioMérieux), L-glutamine (bioMérieux), sodium pyruvate (Boehringer), 100x nonessential amino acids (Boehringer) and AB human serum taken from healthy donors seronegative for all viruses transmissible by known blood derivatives.

Lymphoid cells are cultured in 75-cm² Primaria culture flasks (Falcon) after being separated from plasma and the other formed blood elements by centrifugation on a Ficoll (Lymphoprep®, Flow) gradient. To obtain these lymphoid cells, 50 ml of blood are drawn by venous puncture into a heparinized sterile tube (heparin lithium). The blood and the heparin are mixed well as soon as the blood is drawn. Alternatively, the blood may be drawn into tubes containing EDTA. it is then important to transport immediately the tubes maintained at +4° C. to the laboratory, where they will be handled under a "biohazard" laminar flow culture hood under sterile conditions. For each sample drawn, an "RPMI" medium is prepared which may advantageously comprise 100–150 ml of RPMI 1640 medium, a mixture of penicillin and streptomycin, 4% of L-glutamine, 1% of sodium pyruvate, 1% of Boehringer (100x) nonessential amino acids, as well as 3 sterile 50-ml conical-bottomed tubes (Falcon) containing 10 ml of the "RPMI" medium described above and 4 sterile 50-ml tubes with 20 ml of Ficoll at the bottom. The heparinized tubes are opened in order to pipette the blood, deposit it in the tubes containing medium and mix it gently with the medium described above. 5 ml of "RPMI" medium are taken and the wall of the heparinized tubes is rinsed. It is necessary to accompany this rinse by a gentle scraping using the end of the plastic pipette in order to detach cells which have possibly adhered to the walls of the tube, and to deposit it [sic] in the tubes containing the blood diluted in the "RPMI" medium, mixing the contents gently by successive aspirations/expulsions. These operations should be repeated until the heparinized tubes are clean. The blood diluted in the "RPMI" medium should then be deposited very gently (without disturbance) on the surface of the Ficoll in the 50-ml tubes, and "RPMI" medium should then be used to rinse the remaining diluted blood and recover it as above so as to deposit it with great care on the surface of the tubes with the Ficoll. Thereafter, and without shaking the Ficoll, the tubes should be placed in centrifuge buckets, water-filled tubes should be used for balancing and centrifugation should be carried out at +15° C. for 20 minutes at 1800 rpm, with a slow deceleration mode. After centrifugation, the tubes are recovered, a pipette is inserted gently into them to the depth of the upper "Ficoll/plasma" interface, and the whitish layer located above the Ficoll is aspirated gently while describing concentric circles from the walls, and then describing "zig-zags" from one side to the other of the Ficoll surface. The aspirated medium is placed in 50-ml tubes, diluted in at least 3 times the volume of RPMI medium and mixed gently by inversion of the tubes which have been stoppered under sterile conditions. The tubes are then centrifuged at +15° C. for 10 minutes at 1800 rpm, with a slow deceleration mode. After centrifugation, the supernatant in these tubes is discarded by pouring slowly but evenly, taking care that the whitish cell pellet does not become detached. The pellet is resuspended in 10 ml of "RPMI" medium by successive aspirations/expulsions, and the suspension is centrifuged at +15° C. for 10 minutes at 1800 rpm, with a slow deceleration mode. For each sample or for every 50 ml of blood drawn, two small 75-cm$^2$ electropositive plastic culture flasks (Falcon "PRIMARIA"), and 10 ml of "RPMI" medium to which 15% of "AB" human serum (HS) described above has been added, are prepared. After centrifugation, the supernatant is removed as above, the pellet is resuspended gently 5 ml of "RPMI" medium with 15% of HS and the resuspended cells are distributed in the flasks, which are placed flat and barely raised. The suspension is immediately distributed by moving each flask in the flat position. The centrifugation tubes are rinsed with 5 ml of "RPMI" medium containing 15% HS, and the suspension is added and distributed in the two flasks as above. Advantageously, all the media used for these steps are at 37° C. (warmed on a water bath). When the flasks have been closed, they are kept flat in a humid incubator at 37° C. with 5% of $CO_2$ until the following morning. The following morning, all the supernatant with the cells in suspension should be thoroughly aspirated, and flasks should be rinsed twice with 4 ml of RPMI alone, allowing 5 minutes each time for "soaking" and standing the flask up slowly before aspirating all the remaining medium in order to remove nonadherent cells. The flasks are then filled with 5 ml of RPMI medium containing 15% of HS and are replaced in the incubator, and care is taken not to disturb them for 4 h. From this step onwards, the flasks placed upright should always be filled by directing the jet on to the upper wall in order not to detach the cells which are in the process of adhering, and then, subsequently, affected by a possible cytopathogenic effect. The cell suspensions thus collected 24 h after setting up the culture are centrifuged at +15° C. for 10 minutes at 1800 rpm, with a slow deceleration mode. Where appropriate, the cell pellet may be taken up in fetal calf serum with 10% of DMSO (dimethyl sulfoxide) and frozen at −80° C. or in liquid nitrogen according to a procedure for maintaining viable cells. The corresponding supernatant is then centrifuged at 3000 rpm for 30 min. in order to remove cell debris, and the clarified supernatant is aliquoted, listed as a sample at 24 h of culture, that is to say D1, and then stored in the freezer at −80° C. After 48 h in the incubator, the flasks are taken out, and the supernatant is aspirated with great care and, as above, centrifuged at 3000 rpm for 30 minutes in order to remove cell debris. The clarified supernatant is aliquoted, listed as a sample at 3 days of culture, that is to say D3, and then stored in the freezer at −80° C. The flasks are immediately filled with 5 ml of RPMI medium containing 5% HS and replaced in the incubator. From this point onwards, the culture medium now contains only 5% of HS, and this proportion will be used for all the renewals of medium. The media in the flasks are then withdrawn, stored in aliquots of medium cleared of cell debris, at −80° C. as above, and replaced by "RPMI" medium containing 5% of HS every three or four days until there no longer persists any adherent cell in the flask causing refraction on microscopic observation.

Example 2

Cytotoxicity Test on Cultures of Explants of Rat Embryonic Cerebral Cortex and Explants of Rat Embryonic Spinal Cord Cultures of explants of rat embryonic cerebral cortex are obtained from brains of rat embryos taken from pregnant rats at the fourteenth day of embryonic life. After dissection, the brains are rinsed three times in "Dulbecco-Phosphate Buffer Saline [lacuna] (D-PBS: $KH_2PO_4$ 0.2 g/l, $Na_2HPO_4·7H_2O$ 1.15 g/l, NaCl 8 g/l, KCl 0.2 g/l) buffer, and then in F12 medium (Boehringer). After the meninges have been removed with great care and the cortex isolated, the latter is broken up mechanically using scissors in F12 medium. Concomitantly, spinal cord explants were prepared and cultured according to the same principle. The volume is then adjusted to 30 ml of the F12 medium supplemented with 7.5% of fetal calf serum and 7.5% of horse serum. After 10 minutes of settling, the supernatant is centrifuged for 5 minutes at 4000 rpm. The pellet obtained is suspended in 10 ml of complete medium. The cells are plated out at a density of $10^6$ cells per sterile dish 35 mm in diameter (Falcon) and maintained at 37° C. under 7.5% of $CO_2$ and at 95% humidity. Alternatively, slides with culture cavities of the Labtek® type may be used, in particular for a subsequent immunohistochemical study, after fixing the culture at the requisite time. The culture medium is changed every three days. Usually after 3 to 7 days, when a good differentiation of the cortical neurons is obtained with a well-balanced organization of the underlying lawn of glial and leptomeningeal cells (a little pia mater remains associated with the sample of cerebral tissue used), the cultures are used for cytotoxicity tests with respect to cells of the central nervous system.

The test samples are heated for 30 min at 56° C. in order to inactivate complement proteins and a possible enveloped virus, and then centrifuged for 10 minutes at 1500 rpm. Where appropriate, the recovered supernatant is dialyzed at 40° C. in twice 20 volumes of D-PBS buffer, a first time for 2 h and a second time overnight. The test sample is aliquoted and stored at −20° C. An aliquot is thawed for the cytotoxicity tests and mixed according to the desired dilution with the culture medium of the target cells, and the mixture is replaced in the incubator. In this instance, the target cells consist of all of the cells present in the culture of the explant of cerebral tissue.

A considerable cytotoxic effect was observed under these conditions with supernatants diluted to ¼ in the culture medium of the explants described above, and sampled between the third and the tenth day of culture of blood monocytes from patients suffering from MS in acute exacerbation. This effect was observable under the light microscope used for examination of the cells in culture, from the sixth hour following the introduction of the diluted sample into the culture medium. The effect was first significant in the glial cells, identified by their altogether typical morphology during a regular observation of the culture. A swelling of the oligodendrocytes, which ended up by rounding off and detaching themselves from the culture support, was thus observed, together with a vacuolization of the astrocytes accompanied by a considerable regression of their cytoplasmic processes. At this stage, the neurons present in the culture were relatively well preserved and do not display significant adverse change. Subsequently, after approximately 24 hours under these conditions, the glial lawn being completely destroyed, the neurons ended up by degenerating and detached themselves, in their turn, from the culture. After 48 hours under these conditions, almost no more viable cells remained in the culture wells brought into contact with the supernatants ranging from D3 to D12, whereas the effect of the supernatants of the same cultures of monocytes from MS in acute exacerbation, sampled on D1, D18 or D21, displayed a lesser or even nonexistent effect [sic]. The culture supernatants of blood monocytes/ macrophages from a few controls not suffering from MS did not, in parallel, induce any cytotoxic effect under the same conditions.

Example 3

Cytotoxicity Test on Cultures of Explants of Rat Embryonic Brain

Culture supernatants of monocytes/macrophages from MS in acute exacerbation or from a healthy control were diluted to ¼ in the culture medium of the brain explants of rat embryos which had reached an advanced stage of differentiation of the neurons, and then incubated at 37° C. as described above. An example of the cytotoxic effect described above observed under a light microscope in the cultures of embryonic explants is shown in FIG. 1. Photograph A shows a brain cell culture incubated for 48 h with a sample taken at D6 originating from a healthy control. Photographs B and C show two brain cell cultures incubated for 24 h with two samples taken, respectively, at D18 and at D6, originating from the same culture of monocytes/ macrophages from MS in acute exacerbation. Photograph D shows a brain cell culture incubated for 48 h with a sample taken at D6 originating from the same culture of monocytes/ macrophages from MS in acute exacerbation as for photograph C.

Figure 1A:
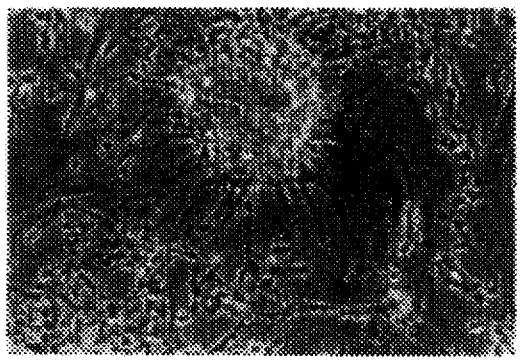
FIG. 1 illustrates the cytotoxic effect, observed under a phase contrast light microscope, in cultures of rat embryonic brain explants.
Figure 1B:
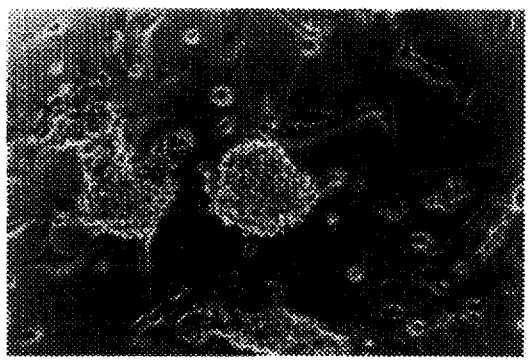
Figure 1C:
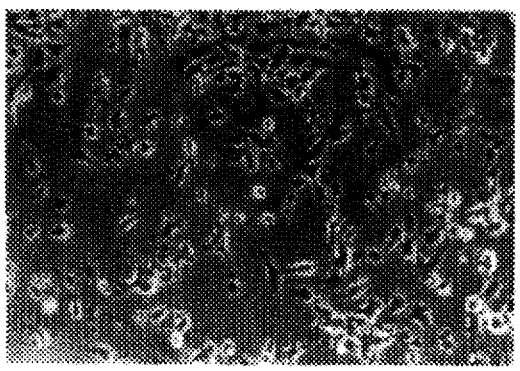
Figure 1D:
Figure 2A:
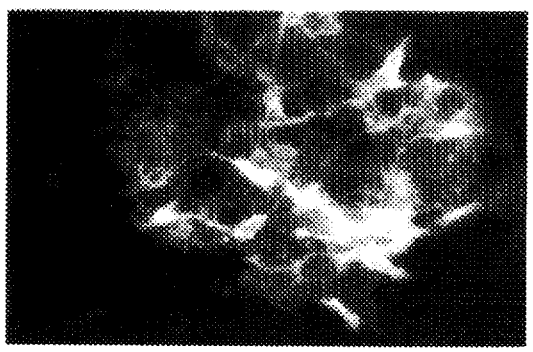
FIGS. 2 and 3 show the cytotoxic effect observed on different cell types present in the cultures of embryonic explants, by immunocytological analysis using a fluorescence microscope at a suitable wavelength for detecting a signal emitted by a secondary antibody used in an indirect immunofluorescence procedure and labeled with fluorescein.
Figure 2B:
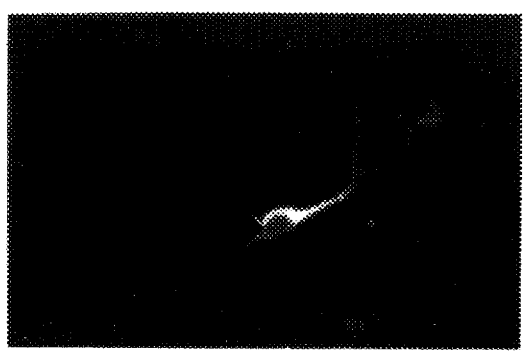
Figure 2C:
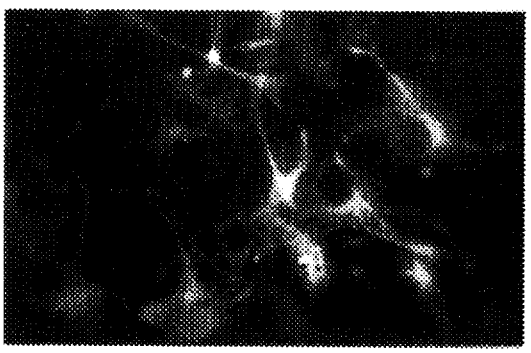
Figure 2D:
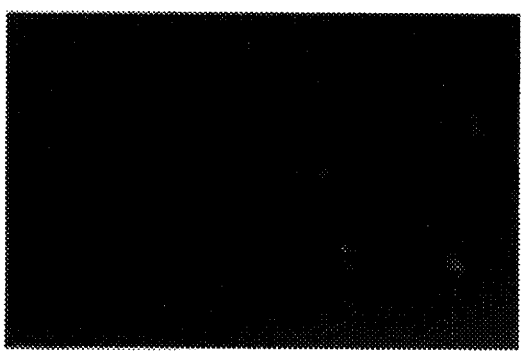
Figure 3A:
Figure 3B:

Moreover, an example of the effect observed on the different cell types present in the cultures of embryonic explants, by immunocytological analysis using a fluorescence microscope, is shown in attached FIGS. 2 and 3. In this example, the supernatants of cultures of monocytes/ macrophages from MS in acute exacerbation or from a healthy control were diluted to ¼ in the culture medium of explants of brain or of spinal cord of rat embryos, cultured on Labtek® slides as described above. The slides were fixed at the requisite time, after two washes in PBS, by incubation for 10 minutes in a mixture of equal volumes of acetone and methanol at −20° C., and then incubated overnight at +4° C. with the appropriate dilution of a first antibody specific for the cell type to be labeled, that is to say an anti-neurofilament antibody (Boehringer anti-NF antibody) for neurons, an anti-glial fibrillar acid protein antibody (Boehringer anti-GFAP antibody) for astrocytes and an anti-myelin basic protein antibody (Boehringer anti-MBP antibody) for oligodendrocytes. After two 10-minute washes in PBS followed by a 5-minute wash in distilled water, the slides were incubated for one hour at room temperature in an appropriate dilution of a second antibody, specific for the immunoglobulins of the species used for producing the first antibody, and coupled to a fluorochrome. After washing the slides as above, the latter were mounted for examination under a fluorescence microscope with the appropriate wavelength. In FIG. 2, photographs A and B show, magnified 40 times, the labeling with an anti-neurofilament antibody of a spinal cord explant incubated with a culture supernatant of monocyte/macrophage from MS in acute exacerbation, sampled at D9, for 12 and 48 hours, respectively. In FIG. 2, photographs C and D show, magnified 40 times, a spinal cord explant incubated for 24 hours with a culture supernatant of monocyte/macrophage from MS in acute exacerbation, sampled at D9, and labeled with an anti-neurofilament antibody and an anti-GFAP antibody, respectively. In FIG. 3, photographs A and B show, magnified 40 times, a spinal cord explant incubated for 24 hours with a culture supernatant of monocyte/macrophage from MS in acute exacerbation, sampled at D6, and labeled with an anti-MBP antibody and an anti-GFAP antibody, respectively.

The earliest and largest cytotoxic effect in these primary cultures of cells of the central nervous system hence manifestly relates to the macroglial cells, namely astrocytes and oligodendrocytes.

Example 4

Cytotoxic and Reverse Transcriptase Activities

The monocyte/macrophage culture protocol having first been developed for studying a retroviral expression in MS (45), the reverse transcriptase activity was tested in a few supernatants according to the conditions previously determined for the study which formed the subject of the investigations of Perron H. (44), in parallel with their cytotoxic activity towards brain cells cultured as explants as described above. In a few MS monocyte/macrophage culture supernatants sampled between D1 and D22, a relative coincidence is observed between the maximum gliotoxic activity occurring in the culture supernatants and the peak of reverse transcriptase activity. However, since neither heating for 30 minutes at 56° C. nor two cycles of freezing/thawing nor removal of the pellet sedimented by ultracentrifugation at 100,000 g for 2 hours impaired the cytotoxic effect of the supernatants analyzed, a direct effect due to infection of the explanted cells by a retrovirus present in the MS monocyte/ macrophage culture supernatants is implausible.

Figure 4:
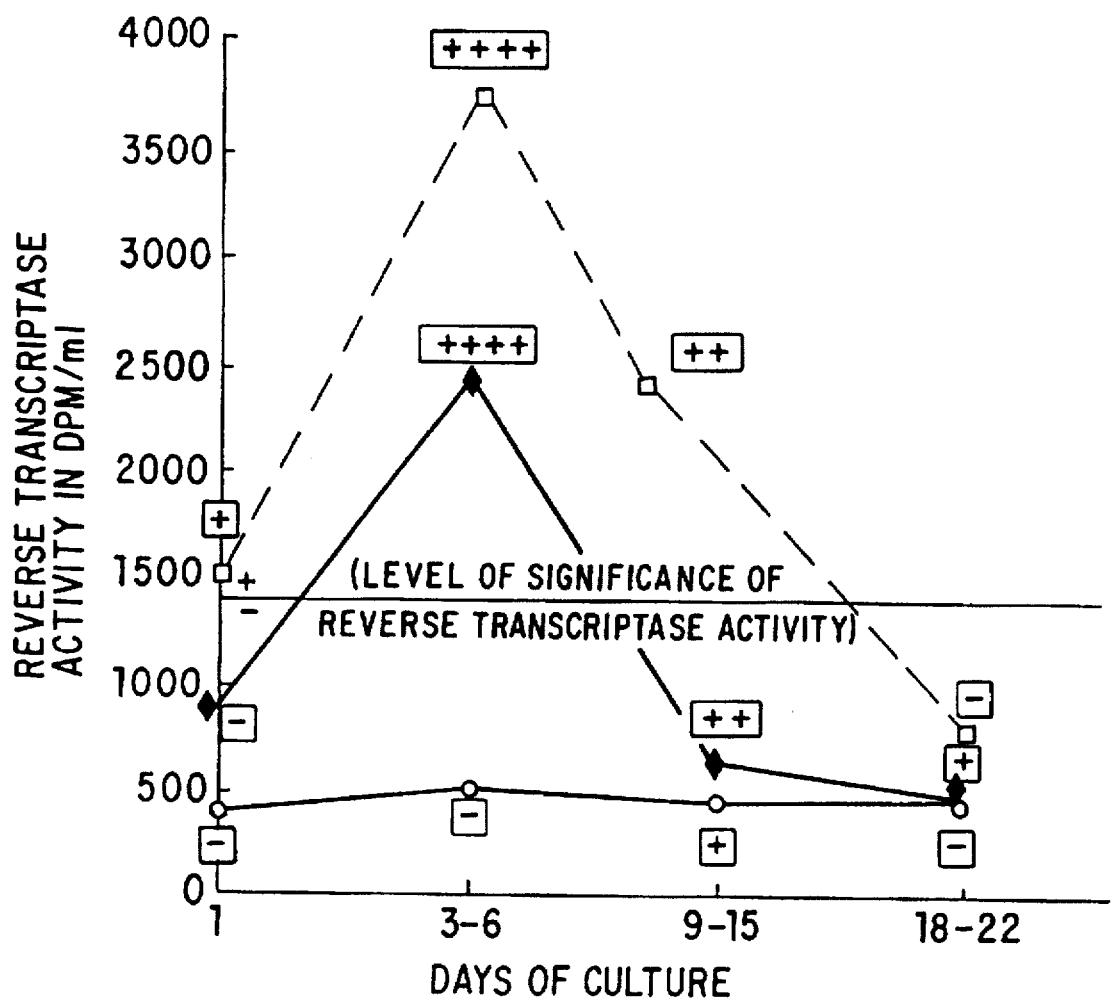
FIG. 4 illustrates the coincidence, in a few cultures of multiple sclerosis monocytes/macrophages, between the reverse transcriptase and cytotoxic activities. The reverse transcriptase activity is given in dpm (disintegration per minute) as a function of the number of days of culture. The curve plotted as a broken line represents a culture of monocytes/macrophages from a patient having a strongly progressive chronic form of MS, the continuous curve with black diamond symbols represents a culture of monocytes/ macrophages from a patient having a remitting form of MS in acute exacerbation, and the continuous curve with open circles represents a culture of monocytes/macrophages from a patient having a remitting form of MS in a period of remission. Cytotoxic activity is represented by a number of plus signs ranging from one to four (positive cytotoxic effect ranging from very weak to very strong) or a minus sign (absence of cytotoxicity) opposite the point plotted on the curve representing the reverse transcriptase activity of the corresponding supernatant.

The relative coincidence, in a few MS monocyte/ macrophage cultures, between the reverse transcriptase and cytotoxic activities shown in FIG. 4. MS monocyte/ macrophage culture supernatants were diluted to ¼ in the culture medium of brain explants, and incubated for 24 hours according to the protocol described above before estimating the cytotoxic effect by microscopic quantification of cell depletion. These results show a relative coincidence between reverse transcriptase activity and the observed cytotoxic activity.

Example 5

Cytotoxicity/Gliotoxicity Tests

In view of the results described above, a standardized system for studying and quantifying the observed cytotoxic effect was sought. After several evaluations, it was found that continuous cultures of immortalized astrocytes (50) constitute an appropriate material for detecting and quantifying, on pure and homogeneous glial cells, a cytotoxic activity such as is described above.

Thus, the continuous astrocyte line is maintained in DMEM-F12 (1:1) medium supplemented with 10% of FCS (fetal calf serum) in an incubator with 7.5% of $CO_2$, at 37° C. and at 95% humidity. The cells are cultured in culture plates or flasks, previously coated with poly-L-lysine at a concentration of 5 µg/ml in PBS. The passage density is, in general, $2 \times 10^3$ cells/cm$^2$. Under these conditions, the cells are cultured for two days, or until a homogeneous monolayer cell lawn is obtained, before being used for the cytotoxicity tests. They may advantageously be cultured on 24-well culture plates, thereby making it possible to work in series on numerous tests to be performed. For the subsequent studies on slides, they may be cultured on Labtek® type cavity culture slides. Generally speaking, samples originating from biological fluids to be tested are heated at 56° C. for 30 min. in order to inactivate complement proteins and a possible enveloped virus, and then centrifuged for 10 minutes at 1500 rpm, and the supernatant recovered.

Each sample is then diluted in the requisite proportion in the DMEM-F12 (1:1) culture medium containing 10% of FCS of the abovementioned astrocytes, and the medium homogenized by pipetting or gentle agitation is deposited in the culture flask or well as replacement for the maintenance medium. The cells are then replaced in the incubator under the conditions described above. The cytotoxic effect with respect to glial cells, represented by astrocytes, is thus assessed in terms of gliotoxic activity.

The gliotoxic effect of the dilutions of the test samples was measured by three different techniques which proved to be concordant.

The first technique, known as "L/D" test, (living cells/ dead cells test), is a rapid, semiquantitative colorimetric assay permitting simultaneous determination of living and dead cells. Living cells are distinguished by the presence of an intracellular esterase activity. The esterase activity is detected by a green fluorescence generated by enzymatic hydrolysis of a substrate, calcein-AM. Dead cells are distinguished by a labeling in the nucleic acids with ethidium homodimer, and only the nuclei of cells whose nuclear membranes are damaged fluoresce red. After 72 h of incubation at 37° C., the cells are rinsed in D-PBS buffer, and incubated for 15 minutes at room temperature and protected from light in the presence of 200 µl of PBS solution containing 2 µM calcein-AM and 4 µM of ethidiumhomodimer. Observation of the cultures with a fluorescence microscope is then performed shortly thereafter. Green (living) and red (dead) cells are counted simultaneously on the see field of observation. Several fields are observed (at least three), and the mean of the counts for the dead cells and for the living cells is taken as the result. The gliotoxic (or, more generally, cytotoxic) activity is expressed according to the formula: % cytotoxicity =(mean number of dead cells/ mean number of living cells) ×100.

The second technique consists of a colorimetric assay of living cells using methyltetrazolium bromide (MTT) is a salt used for a quantitative colorimetric assay (51). MTT is a substrate for mitochondrial dehydrogenases which, after reduction in metabolically active cells, gives a colored product, formazan (violet). It thus enables living cells to be labeled. Cells ($2 \times 10^3$ cells/cm$^2$) are exposed for 72 hours to different dilutions of purified fractions (3 wells or dishes per dilution to be tested). They are then rinsed in D-PBS buffer and thereafter incubated for 3 h at 37° C. in 3 ml of MTT solution at a concentration of 0.5 mg/ml in DMEM-F12 (1:1). The supernatant is removed and acid isopropanol ($4 \times 10^{-2}$ M HCl) is applied to the cells in order to solubilize the formazan crystals. The resulting lysate is centrifuged for 2 min/6500 rpm in order to remove cell debris. An optical density reading is then performed at 570–630 nm.

The third technique employs a radioactive assay with $^{51}Cr$ which permits the quantification of dead cells. $^{51}Cr$ is a radioactive element capable of entering living cells and which is released into the extracellular medium only when the cells die. The measurement of incorporated radioactivity, after washing the cells brought into contact with a medium containing $^{51}Cr$, as well as that released by the cells into the medium, will permit a quantification of the living and dead cells. Astrocytes ($2 \times 10^3$ cells/cm$^2$) are incubated for 2 h at 37° C. in DMEM-F12 (1:1) medium containing 20 µCi of $^{51}Cr$. The cells are then rinsed 3 times in DMEM-F12 medium, exposed to different dilutions of purified fractions (3 wells or dishes per dilution to be tested) and incubated for 72 h at 37° C. The supernatant is recovered and the cells lysed with 1M NaOH solution. Counting, in counts per minute (cpm), of the radioactivity (gamma counter) present in the supernatant and in the lysate is then performed, and a percentage cytotoxicity is determined, calculated in the following manner: % cytotoxicity=[(cpm supernatant– natural cpm)/(total cpm–natural cpm)]×100. The natural radioactivity in cpm corresponds to the background measured by the counter on a sample originating from a culture incubated with the same, nongliotoxic fluid (CSF, serum or monocyte/macrophage culture supernatant) and with $^{51}Cr$, under the same conditions as the test sample.

For reproducibility and reliability studies, several wells were incubated with the same dilution of the same gliotoxic sample, and the standard deviation obtained was taken into account for the significance of the results of the subsequent series of analyses. This type of verification may be performed with each change of batch of astrocytic cells (thawing of a new ampoule) or with each change of batch of culture medium (batch of FCS most particularly). In the experiments mentioned here, a percentage of dead cells of greater than 5% proves to be indicative of a cytotoxic effect which is absent under normal culture conditions.

Example 6

Kinetics of Cytotoxic Activity

MS monocyte/macrophage culture supernatants which were cytotoxic on primary cultures of embryonic brain explants, as well as noncytotoxic control supernatants, were tested on cultures of the abovementioned astrocyte line. The presence of gliotoxic activity detected by the astrocytes and visualized by the "L/D test" was to be found in the supernatants which were previously cytotoxic for the primary cultures and not in those which had not had this property. It was thus possible to study the kinetics, during the maintenance of monocytes/macrophages in culture, of the expression of gliotoxic activity in the supernatants of cultures originating from patients suffering from MS and from controls. It was thus possible to verify that this activity was not detected at any time in the cultures originating from healthy controls, and also that its intensity fluctuated with time in the "positive" cultures originating from patients suffering from MS. In effect, several peaks of activity one [sic] been able to be observed in the few cases studied. These peaks lay, in general, between the 6th and the 9th and then between the 15th and the 18th day of culture (D6 to D9 and D15 to D18), thus indicating an active synthesis in the culture, since the supernatant is completely withdrawn therefrom twice weekly at each change of culture medium.

Figure 5:
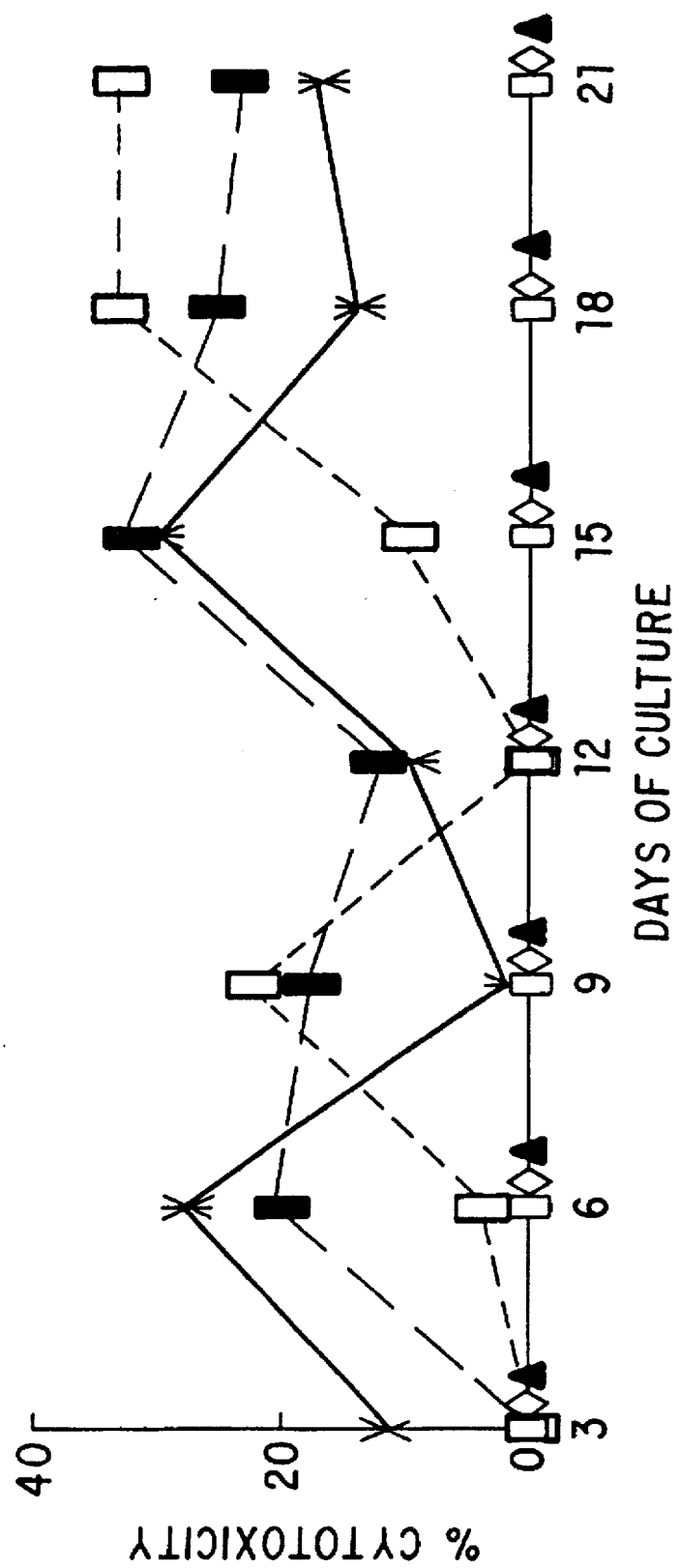
FIG. 5 illustrates, as a function of the days of culture, the kinetics of the expression of cytotoxic activity from culture supernatants originating from patients suffering from MS and from controls. On the graph, the three curves in continuous or broken lines show the kinetics of gliotoxicity in the culture supernatants of monocytes/macrophages from three different cases of MS, and the points aligned on the abscissa axis (black triangle, open diamond and open rectangle) the negative kinetics of culture of monocytes/ macrophages from three controls suffering from other neurological diseases.

An example of such an observation, carried out by means of the use of the biological test developed, is shown in FIG. 5. In this example, the supernatants of MS monocyte/macrophage cultures were treated and used as described above for the cytotoxicity/gliotoxicity tests on the above-mentioned astrocyte line with a dilution to 1/10 in the culture medium, and incubated for 72 hours according to the protocol described above with measurement of the gliotoxic effect by the "L/D test" method.

Example 7

Demonstration of a Gliotoxic Activity in Biological Fluids of Patients Suffering from MS Subsequently, this biological test was used to test for possible gliotoxic activity in the cerebrospinal fluid (CSF) and the serum. Thus, the inventors were able to demonstrate significant gliotoxic activity in the CSF of patients suffering from MS, and not in CSF of controls suffering, for example, from normal pressure hydrocephalus (NPH). The same finding was made with the corresponding sera, albeit with a relatively lower gliotoxic activity than in the CSF, thereby supporting the view of an intrathecal production of the factor bearing this activity.

Figure 6A:
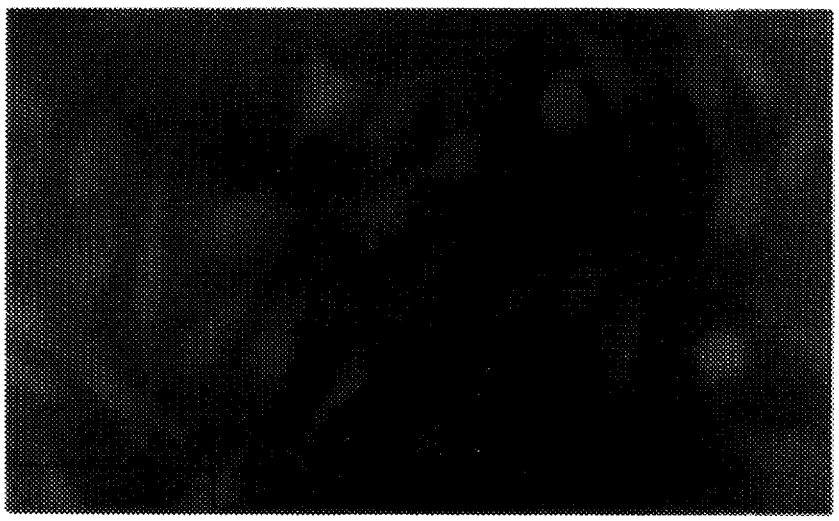
FIG. 6 shows a visualization of living and/or dead astrocytic cells with an optical system.
Figure 6B:
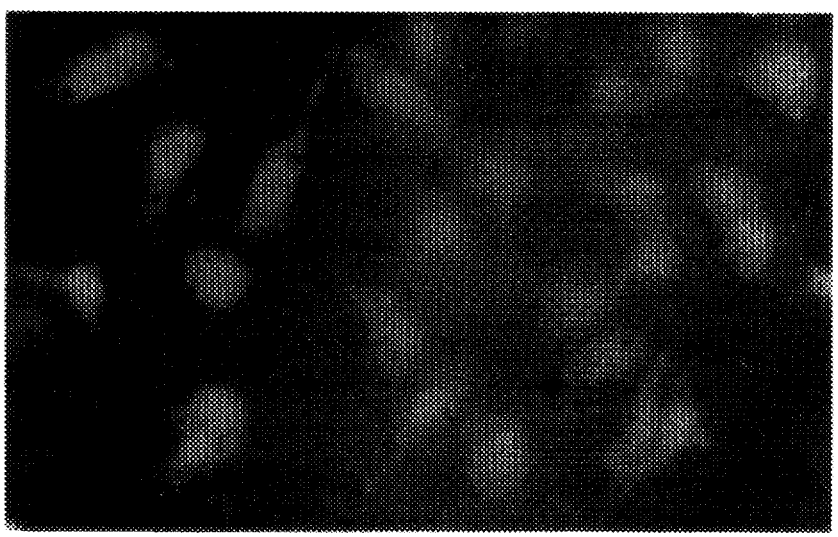
Figure 6C:
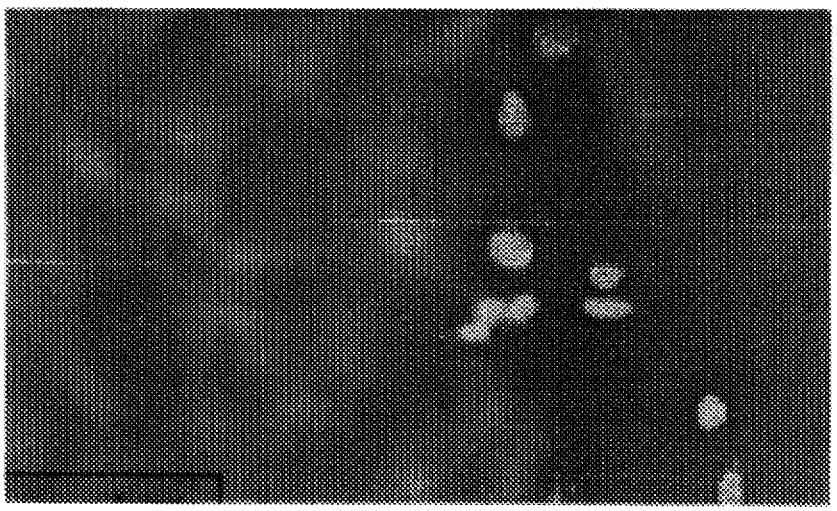
Figure 7A:
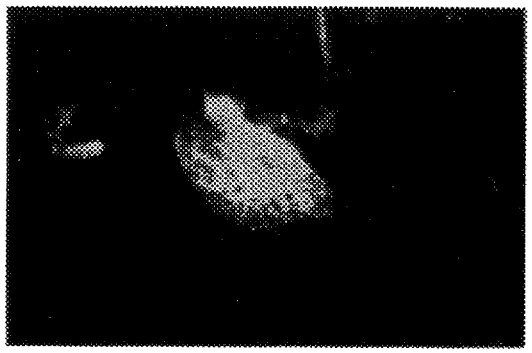
FIG. 7 shows the cytological effects linked to cytotoxicity on astrocytes.
Figure 7C:
Figure 7B:
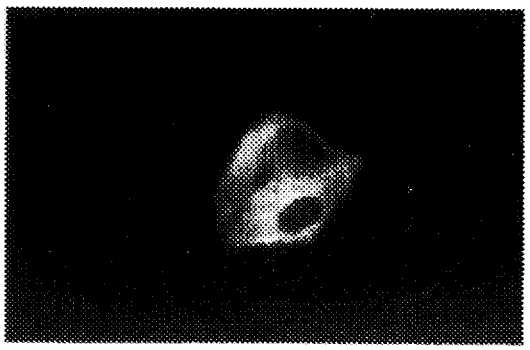
Figure 7D:
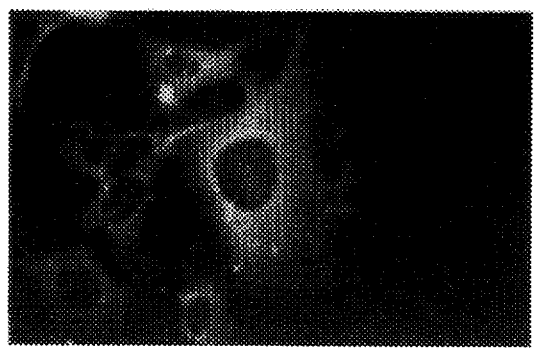

An example of the use of the "L/D test" for visualizing the detection by astrocyte targets of a gliotoxic factor in the samples mixed with the culture medium is shown in attached FIG. 6. In this example, a CSF from remitting MS in exacerbation was diluted to 1/10 in the culture medium, incubated for 72 hours and examined with a fluorescence microscope, the entire procedure being according to the protocol described above for the "L/D test" Photograph A shows a visualization of the living cells with an appropriate optical system for the light emissions from fluorescein (the bar represents 25 micronmeters [sic]). Photograph B shows a visualization of the dead cells with an appropriate optical system; the bar represents 25 micronmeters [sic]. Photograph C shows a simultaneous visualization of the living and dead cells with an appropriate optical system for the light emissions from the two fluorophores (485–500 nm); the bar represents 25 micronmeters [sic].

Once this quantification test had been developed, the inventors analyzed filters prepared by the firm Pall and used in therapeutic trials on patients suffering from MS (52). These trials consist in filtering the cerebrospinal fluid through filters having, in particular, an affinity for glycoproteins and selected by the company PALL. Filters were obtained after filtration of the CSF from a few cases of MS, and the proteins adsorbed to the filters were redissolved using a solution containing 1% of SDS. After the samples were brought to physiological conditions, it could be shown that a strong gliotoxic activity, evaluated by the present biological test on an astrocyte line, is associated with the proteins previously retained on these filters.

An example of the use of the biological test for detecting and quantifying gliotoxic activity in biological fluids, in particular in the CSF of patients suffering from MS, is presented in attached Table 1, where the effects of the filtration of the CSF through the filter supplied by the company PALL are shown.

In this table, the CSF were filtered through PALL filters having the same type of filtration medium as those used in vivo in therapeutic trials. The gliotoxic activity of each filtrate, measured according to the biological test on astrocytes, and the result in comparison with the gliotoxic activity of the native CSF before filtration, with the statistical significance of the difference observed on a series of 10 measurements, are presented therein. In this example, the CSF were diluted to 1/10 in the culture medium and incubated for 72 hours according to the protocol described above for the "L/D test". The mean value of the percentage of dead cells was obtained, for each sample, on 5 fields chosen at random on two wells incubated in parallel with the same sample. A statistically significant difference exists between the MS CSF and the filtrates obtained after filtration. The diagnoses of MS are, except where otherwise stated, diagnoses of definite MS according to the criteria of Poser (49).

This example shows that physicochemical means exist for removing at least part of said gliotoxic factor from the biological fluids of patients suffering from MS, or from other diseases in which said gliotoxic factor or alternatively said gliotoxic activity might be detected in vivo. These results also confirm the molecular reality of said gliotoxic activity, as well as the importance of the detection and assay techniques which are subjects of the present invention.

Another example of the use of the biological test developed by the inventors, for detecting and quantifying gliotoxic activity in biological fluids, in particular in the CSF of patients suffering from MS, is presented in attached Table 2. In this example, the CSF were diluted to 1/20 in the culture medium according to the protocol described above for the colorimetric MTT test, and incubated for 96 hours. Each result represents the mean of two separate experiments each representing a series of 5 independent wells, that is to say, finally, a mean of 10 values per CSF tested.

The CSF samples originating from patients suffering from a remitting form of MS were taken at the time of clinical exacerbations. The difference in the mean cytotoxicity values in the two subpopulations of MS, remitting versus progressive chronic, is statistically significant, indicating in principle that the quantification of the gliotoxic activity of the CSF enables the clinical activity of the disease to be correlated. The diagnoses of MS are, except where otherwise stated, diagnoses of definite MS according to the criteria of Poser (49).

The results presented in Tables 1 and 2, together with other similar results, thus enabled the inventors to demonstrate the existence of very significant gliotoxic activity in the CSF of patients suffering from MS, and a variation of its intensity in accordance with the clinical state and/or the mode of progression. These results confirm the importance of the biological test developed on an astrocyte line, in combination with a quantification technique which can be, for example, one of the three techniques described above ("L/D test", MTT colorimetric assay and $^{51}$Cr-release assay), in studies to determine prognosis and/or in the therapeutic monitoring of pathologies in which such a cytotoxic, and in particular gliotoxic, activity may be detected, or even in the diagnosis of a disease such as MS.

Example 8

Cytotoxic Activity Observed on Other Cell Types

Moreover, the specificity of the observed cytotoxic activity was also evaluated, and quantified by the "L/D test", on cultures of various other cell types. With samples which had previously been shown to be cytotoxic with respect to glial cells, either in culture of rat embryonic brain explants or on the astrocyte line, no direct cytotoxicity was detected on fibroblasts, myoblasts and mouse leg muscle cells and on endothelial cells. A markedly lower cytotoxicity, of approximately 10% relative to the abovementioned astrocytes, was observed on sciatic nerve Schwann cells. It is of interest to note here that the Schwann cells are responsible for the myelination of peripheral nerves, just as the oligodendrocytes are responsible for normal myelination in the central nervous system. In the cultures of embryonic brain explants, the few leptomeningeal cells present do not appear to be directly affected, and the same applies to the neurons, which appear to be affected only after considerable modification of the nutritive lawn of glial cells. Blood monocytes set up in culture and which have differentiated into macrophages after adhering to the culture support do not appear to be affected either, since they persist in culture even in the presence of several successive peaks of gliotoxic activity released into the supernatant in the course of macrophage culture (see FIG. 5). As regards lymphocytes, contradictory results have been obtained with cultures of cells expressing the CD4 antigen, namely, with the same gliotoxic sample compared with the seine nongliotoxic control sample, significantly increased cell death was observed in some cultures, whereas a cell proliferation was observed in cultures originating from other lymphocyte-donor individuals.

These observations on lymphocytes have similarities with the effects described for molecules having superantigenic properties (26, 27).

Example 9

Cytological Characterization of the Cytotoxic Effects

These data obtained with lymphocytes led the inventors to clarify beforehand the cytological effects linked to the cytotoxicity, on the astrocytes used in the biological tests for gliotoxicity. A study of the intermediate filaments of the abovementioned astrocytes revealed a considerable effect of gliotoxic fluids on the organization of the astrocyte cytoskeleton, after incubation of the cells according to the protocol described above for the gliotoxicity tests. In effect, whereas no modification is observed with the nongliotoxic control fluids tested in parallel, a drastic disorganization of the vimentin and GFAP filaments is observed in the cultures of astrocytes brought into contact with significant gliotoxic activity originating from biological fluids from patients suffering from MS (monocyte/macrophage culture or CSF). This phenomenon had also been observed on the primary cultures of embryonic nervous system explants, in which the astrocytes were specifically labeled with an anti-GFAP antibody.

An example of this disorganization of the vimentin and GFAP intermediate filaments on astrocytes in cultures brought into contact with gliotoxic fluids originating from patients suffering from MS is presented in FIG. 7. In this example, the detection of GFAP was performed on a primary culture of cells cultured on Labtek® type slides. After incubation for one hour and 24 hours with the culture medium containing a 1/20 dilution of a gliotoxic MS monocyte/macrophage culture supernatant, the adherent cells on the slide are rinsed twice in PBS and then fixed in 4% paraformaldehyde for 20 min at 37° C. After 2 rinses in PBS, they are incubated for twice 5 minutes in a PBS/1% milk blocking solution. The first antibody is polyclonal, raised in rabbits. The antibody is diluted to 1/50 in the blocking solution. Incubation lasts 1 h at 37° C. After the first incubation, a series of 5-minute rinses in PBS and then in the blocking solution is performed in order to remove unbound antibodies. The visualization system employs fluorescein coupled to an anti-rabbit immunoglobulin diluted to 1/100 in the blocking solution. Incubation lasts 1 h at 37° C. Mounting of the preparations is carried out with moviol in order to avoid a decrease in fluorescence at the time of observation. The slides are stored in darkness at 4° C. Observations are made with a fluorescence microscope. The detection of vimentin was performed on the astrocyte line cultured on Labtek® type slides, after incubation for 24 hours with either a 1/50 dilution of a gliotoxic MS monocyte/macrophage culture supernatant, or a normal culture medium. After 24 hours of incubation, the cells ($1\times10^3$ cells/cm$^2$) are rinsed twice in PBS and then fixed for 10 min at −20° C. with acetone. After 3 rinses in PBS, they are incubated for three times 5 minutes in a PBS/5% FCS blocking solution at room temperature. The first antibody is polyclonal, raised in goats. The antibody is diluted to 1/50 in the blocking solution. incubation is for 2 h at 37° C. After 3 5-minute rinses in PBS and then in the blocking solution, the cells are incubated for 1 h at 37° C. with a second antibody directed against goat IgGs, coupled to fluorescein and diluted to 1/200 in the blocking solution. Photograph [sic] A and B show a labeling of the GFAP after 1 and 24 hours incubation, respectively, in the presence of the diluted gliotoxic sample. Photographs C and D show a labeling of the vimentin of the astrocytes in the line, incubated for 24 hours with a normal medium and a medium containing the diluted gliotoxic sample, respectively.

Furthermore, the inventors studied the appearance of the cellular DNA extracted from cultures of astrocytes cultured in normal medium and cultured for increasing times in the presence of gliotoxic samples originating from MS. It was then found that the DNA originating from cultures subjected to gliotoxic activity displayed a fragmentation of the cellular DNA, the intensity of which increased in accordance with the incubation time of the cells, whereas the DNA of cells incubated in medium without gliotoxic activity remained homogeneous at a very high molecular weight.

These observations are compatible with an apoptosis process such as may be induced by superantigens, on lymphoid cells in particular.

Example 10

Dose-Response Effect

Subsequently, in order to evaluate the possibilirty that this gliotoxic activity detected is borne by a molecule, or by a factor whose molecular representation might prove more complex, present in the fluids tested, the inventors first evaluated, using the biological tests developed and described above, the reality of a dose-response effect on the cytotoxicity induced by reference samples. A dose-response effect compatible with a direct proportionality of cell death with respect to the dilution, and with an effect of saturation of the astrocyte detection system at high concentrations, was observed after visualization of the effect by the "L/D test".

An example of this dose-response effect observed with a gliotoxic biological fluid is presented in FIG. 8. In this example, an MS monocyte/macrophage culture supernatant was mixed, in successive dilutions, with the culture medium of the astrocytes according to the protocol described above for the "L/D test".

In this way, the inventors characterized a cytotoxic, and more especially a gliotoxic, activity in the cultures of blood monocytes/macrophages, CSF and serum of patients suffering from MS, in parallel with the development of a method for detecting said cytotoxic activity on primary cultures of brain and spinal cord explants of rat embryos, and said gliotoxic activity on astrocyte lines in culture, as well as also the development of a method for quantifying said gliotoxic activity, coupled to the detection method on astrocytes in culture.

Their first objective having been the demonstration of this gliotoxic activity in vivo in patients suffering from MS, and the means for its systematic and standardized assay, the inventors then directed their attention to endeavoring to link this activity with a particular molecule, or a factor represented by a set of defined molecules, in the fluids tested.

Example 11

Characterization of the Cytotoxic/Gliotoxic Factor

The inventors first observed that the biological activity defined as gliotoxic activity by the methods described above persisted in gliotoxic samples placed in a water bath at $+56°$ C. for half an hour but was abolished when the temperature was $+100°$ C. for 15 minutes, and persisted after freezing the sample to $-80°$ C. followed by thawing to $+37°$ C. After centrifugation at 100,000 g for 2 hours and removal of the pellet of sedimented material, the activity of samples previously recognized as gliotoxic according to the methods described in the present invention was still present in the supernatant, and hence resembles a nonparticulate soluble factor. Similarly, the incubation of gliotoxic samples in which the total amount of protein has previously been determined by the technique of Bradford (53) in the presence of trypsin, pronase, proteinase K or a mixture of N-glycosidase F and neuraminidase, under sufficient conditions for complete enzymatic hydrolysis of the peptide bonds or of the N-glycosylations present in the sample, does not abolish their gliotoxic activity as is described above.

Subsequently, the inventors carried out the separation and fractionation of the different compounds from samples which had previously proved gliotoxic by the methods described in the present invention. For all of these investigations, the samples are previously heated for 30 min at 56° C. and centrifuged for 10 min at 1500 rpm, and the supernatant is then recovered and, where appropriate, dialyzed at 4° C. in twice 20 volumes of D-PBS buffer, the first time for 2 h and a second time overnight. The supernatant thus collected constitutes the sample on which the different operations are performed. Furthermore, the fractions originating from samples whose molecular components have been separated by different methods are treated so as to remove possible toxic molecules introduced into the media collected by the methods used, and so as to redissolve the organic molecules under physiological conditions compatible with the methods for detecting and quantifying the gliotoxic biological activity as are described in the present invention. To this end, the samples are lyophilized, resuspended in 2.5 ml of sterile distilled water, applied to an NAP-25 type chromatography column (Pharmacia) previously washed in 10 volumes of D-PBS buffer, then eluted with 3.5 ml of D-PBS buffer and used as they are for the gliotoxic activity test.

Thus, to study the ionic charge of the gliotoxic factor as defined above, samples which were gliotoxic according to the criteria defined above and originating from MS monocyte/macrophage culture supernatants and CSF were passed at a flowrate of 60 ml/hour through an FPLC chromatography column of the DEAE-Sepharose CL-6B (Pharmacia) type equilibrated in a buffer A (50 nM Tris-HCl, pH 8.8). Under these conditions, the fraction bearing gliotoxic activity present in the original sample is eluted with an ionic strength of between 0.12M and 0.2M NaCl of buffer A.

To study a possible physicochemical analogy with certain serine proteases which have a strong affinity for liquid chromatography supports of the Blue-Sepharose (Pharmacia) type, samples which were gliotoxic according to the criteria defined above, originating from MS monocyte/macrophage culture supernatants and CSF and previously dialyzed at 4° C. in twice 20 volumes of buffer B (50 mm Tris, pH 7.2) and containing 5 mg of proteins per ml, were applied to an FPLC column of the Blue-Sepharose CL-6B (Pharmacia) type. After elution with 0.1M KCl in buffer B, no gliotoxic activity was to be found in the eluate, whereas the fraction bearing gliotoxic activity was recovered with an activity yield close to 70% by elution with 1.5M KCl in buffer B. Analysis also revealed that serum albumin was also eluted in this same fraction. However, the protease activity of the eluate was tested by incubating the latter with "azocasein" (Sigma) or "azocoll" (Sigma) in D-PBS buffer, pH 7.5 at 37° C. for 2 hours, without it being possible to demonstrate any proteolytic activity of the sample thus prepared and eluted.

To study the possible association of such a gliotoxic factor with IgG type immunoglobulins, samples which were gliotoxic according to the criteria defined above and originating from MS monocyte/macrophage culture supernatants and CSF were applied to an FPLC column of the protein A-Sepharose CL-4B (Pharmacia) type previously washed with 5 volumes of D-PBS. The protein A content of the swollen gel was equal to 2 mg/ml, and the capacity for binding human IgG was of the order of 20 mg of IgG/ml of gel (gel volume 1.5 ml). The fraction lacking IgG was recovered by elution with D-PBS and contained the gliotoxic activity, whereas the fraction enriched in IgG, eluted with 50 mm [sic] glycine-HCl buffer, pH 3.0, did not contain gliotoxic activity as defined above when the samples originated from CSF or from supernatants of monocyte/ macrophage cultures performed under the conditions described above. In the case of samples originating from human sera, a low gliotoxic activity was to be found in the fraction enriched in IgG, this being the case both for sera from MS in exacerbation drawn at the same time as a CSF which proved gliotoxic, and for sera from controls suffering, for example, from normal pressure hydrocephalus (NPH), whose CSF drawn at the same time did not display any gliotoxic activity. However, the study of NPH or of healthy control sera did not reveal any gliotoxic activity in the fraction lacking IgG eluted with D-PBS, whereas almost the whole of the considerable gliotoxic activity of the sera from patient [sic] suffering from MS in exacerbation was to be found in this fraction lacking IgG eluted with D-PBS. This suggests that there is/are one or more gliotoxic component (s) in the serum of healthy individuals which are different from the gliotoxic factor which has been demonstrated by the inventors of the present invention, of markedly lower activity and which is to be found eluted in the fraction enriched in IgG after passage through a protein A-Sepharose column under the conditions described above. This probably resembles a nonspecific gliotoxicity linked to active proteins of serum, as has already been reported (54). However, the small amount of human serum originating from healthy donors having an AB positive blood group present in the monocyte/macrophage cultures does not appear to produce, under these analytical conditions, this additive gliotoxicity collected in this way with the elution of IgG. This may be due to the dilution effect which, as a result of the low activity of this component, renders it undetectable by our methods, or alternatively to an effect of inactivation of this component during the culturing of monocytes/macrophages under the conditions described above. If there is added to this fact the absence of detectable gliotoxicity under these conditions after one and the same analysis of nongliotoxic samples originating from CSF of controls suffering from NPH or originating from culture supernatants of monocytes/macrophages from healthy individuals, these results confirm the novel nature of the gliotoxic activity, and thereby of the associated gliotoxic factor, constituting subjects of the present invention, relative to the gliotoxic activities capable of occurring in the absence of a pathological process in the biological fluids of apparently healthy individuals.

To study the molecular weight of said gliotoxic factor, the inventors concomitantly and successively analyzed samples which were gliotoxic according to the criteria defined above, and originating from monocyte/macrophage culture supernatants, from PALL filters which were used for filtering in vivo the CSF of MS patients and from MS CSF, on an FPLC column of the Superose 12 (Pharmacia) type and on polyacrylamide gel electrophoresis in the presence of SDS (SDS-PAGE). After analysis on a Superose 12 column, the fractions containing gliotoxic activity were eluted after an elution volume corresponding to a molecular weight of approximately 17 KD by matching against the reference curve of the elution volumes of standard globular proteins. More precisely, after collection of fractions which were closer together in this elution zone, two separate peaks of gliotoxicity could be observed, at elution volumes corresponding to a molecular weight of approximately 21 KD and of approximately 16.8 KD. A similar elution of the same sample in a buffer to which 8M urea has been added gives identical results, indicating that there are no multimeric associations of the components eluted under physiological buffer conditions.

After analysis by one-dimensional SDS-PAGE, the protein bands containing gliotoxic activity, after elution from the gel and a return to physiological conditions, were to be found in a portion of gel corresponding to a molecular weight of approximately 17 KD and, under certain conditions of analysis and of content of biological material analyzed, in an additional portion of approximately 21 KD. In parallel, the other protein bands as well as different regions of the gel without proteins were tested, without it being possible to detect any significant gliotoxic activity therein. Two-dimensional analysis of the gliotoxic protein band extracted from the gel at around 17 KD showed the existence of two major spots at 17 KD displaying, between approximately pH 6 and pH 7, a different isoelectric point, and a minor spot at 18 KD having a slightly more basic isoelectric point, above a pH of approximately 7.

Figure 9A:
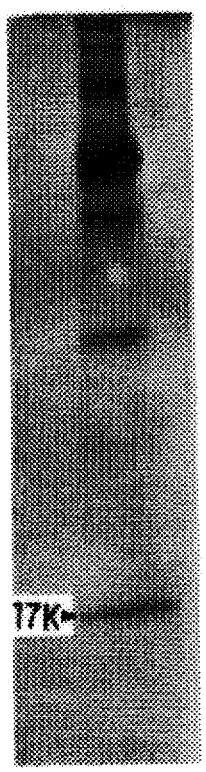
FIGS. 9A and 9B show, respectively, the one and then the two-dimensional acrylamide gel electrophoresis of a gliotoxic fraction obtained from filters used for the in vivo filtration of cerebrospinal fluid (CSF) of patients suffering from multiple sclerosis. Prior to electrophoresis, the molecules adsorbed on the filter were eluted and then passed through an ion exchange resin.
Figure 9B:
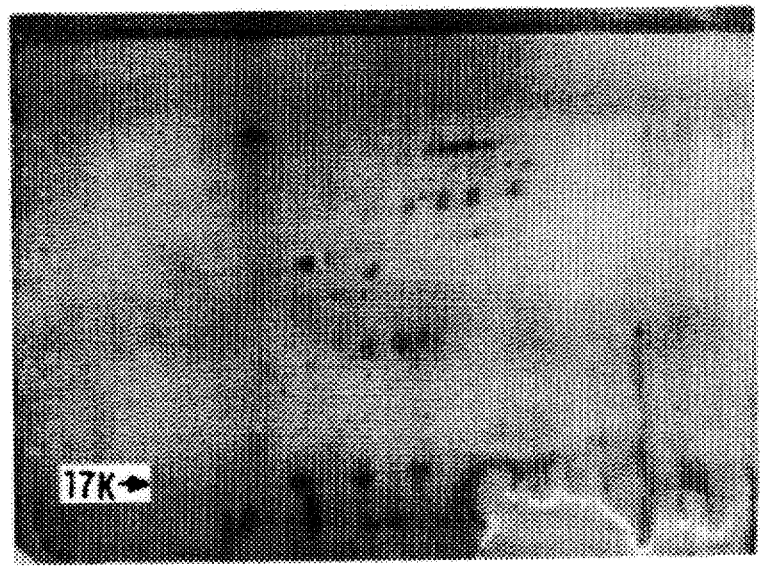

An example of analysis by one- and two-dimensional gel electrophoresis of the protein components of a gliotoxic fraction obtained after passage through a DEAE column is presented in FIGS. 9A and 9B. In FIG. 9A, the photograph may be seen of a Coomassie blue-stained one-dimensional acrylamide gel originating from a mixture of gliotoxic samples eluted from some ten PALL filters which were used for the in vivo filtration of the CSF of a series of patients suffering from MS. These filters are opened mechanically and the filters washed in the presence of 1% SDS, and the eluates are then returned to physiological buffer by means, in particular, of a passage through an NAP-25 column as described above. The filtrates thus treated are tested for their gliotoxic activity on an aliquot, and passed as a mixture through a DEAE-Sepharose column. The fraction containing gliotoxic activity is desalted on an NAP-25 column and concentrated by evaporation before being applied in two parts, one to a one-dimensional SDS-PAGE gel (FIG. 9A) and the other to a two-dimensional SDS-PAGE gel. A photograph of such a two-dimensional gel is presented in attached FIG. 9B. The band visualized with an apparent molecular weight of 17 KD in one dimension proves to be the only protein band visualized bearing gliotoxic activity on the gel shown in 9A, and it may be seen on the two-dimensional gel (9B) that this band of approximately 17 KD separates into three spots of different isoelectric points, the third spot on the right having an apparent molecular weight slightly higher than the two spots at the left.

An example of analysis with a Superose 12 FPLC column is presented in FIGS. 10A and 10B. In this example, culture supernatants of monocytes/macrophages from a patient suffering from MS, sampled between the 6th and the 16th day of culture, representing a volume of 20 ml and 140 mg of proteins, were first passed at a flow rate of 60 ml/hour through an FPLC chromatography column of the DEAE-Sepharose CL-6B (Pharmacia) type equilibrated in a buffer A (50 mM Tris-HCl, pH 8.8). Concomitantly, a Superose 12 column was equilibrated with a buffer C, 50 mM Tris-HCl, pH 6.8, and calibrated by eluting a mixture of globular proteins of known molecular weight in this same buffer C. The fraction theoretically bearing gliotoxic activity present in the original sample was eluted from the DEAE-Sepharose column with an ionic strength between 0.12M and 0.2M NaCl of buffer A, in a volume of 15 ml containing 39 mg of proteins. One third of this fraction, containing 13 mg of proteins, was then applied to the Superose 12 column in a buffer without urea (FIG. 10A), and another third to an identical column in 8M urea buffer (FIG. 10B). During elution in buffer C, 40 fractions were collected, and a continuous measurement of the absorption at 280 nm to assay the proteins in the eluate was recorded with a high sensitivity of detection (R=1.2). The gliotoxic activity of the different fractions collected was tested according to our biological test on an astrocyte line and quantified, after 72 h of incubation, by the "L/D test" technique. To this end, the fractions were lyophilized, resuspended in 2.5 ml of sterile distilled water, applied to an NAP-25 (Pharmacia) type chromatography column previously washed in 10 volumes of D-PBS buffer, then eluted with 3.5 ml of D-PBS buffer and used as they were for the gliotoxic activity test. In FIGS. 10A and 10B, the curve in a continuous heavy line represents the optical density at 280 nm, and the curve in a broken line represents the gliotoxic activity. The correspondences between the elution volume (Ve) and the apparent molecular weight were calculated in accordance with the calibration carried out previously with reference proteins, and is noted at the top of the peaks of gliotoxic activity. It should be noted that a slight gliotoxic activity is to be found in a fraction corresponding to a molecular weight of approximately 110 KD. However, the similarity of the elution profiles in the presence and absence of 8M urea supports the view of a monomeric composition of the factor eluted at these different molecular weights. Accordingly, in this example, the gliotoxic activity specific to the factors of apparent molecular weights approximately 21 KD and approximately 17 KD can be demonstrated and matched to the individual factors.

The results obtained by FPLC chromatography on a Superose 12 column and by electrophoretic analysis show that the gliotoxic factor consists at least of a protein or associated molecule of molecular weight 17 KD and a protein or associated molecule of molecular weight 21 KD. The fact that the apparent molecular weights at which the gliotoxic activity is to be found are identical in both types of technique (FPLC and electrophoresis) suggests that the factors in question are globular proteins. Furthermore, since a comparative study of SDS-PAGE gels in the presence or absence of β-mercaptoethanol gave, moreover, identical migration profiles, these proteins are probably homomers. The fact that the gliotoxic activity is to be found, among all the chromatography fractions and all the portions of gel analyzed, at two different molecular weights of approximately 17 KD and approximately 21 KD may be explained by two molecules without significant homology, or by the existence of glycosylations or of any different post-translational modifications on the same protein substrate, or alternatively by the existence of a propeptide or of a peptide portion of some kind which, after cleavage of a protein of approximately 21 KD, generates a protein of approximately 17 KD.

Thus, to study the possible glycosylation of said gliotoxic factor, samples which were gliotoxic according to the criteria defined above and originating from MS monocyte/macrophage culture supernatants, sera and CSF and from filters which were used for filtering in vivo the CSF of MS patients were analyzed on an FPLC column of the concanavalin A-Sepharose (Con A-Sepharose, Pharmacia) type. For this study, the gliotoxic biological examples were previously passed through an FPLC column of the DEAE-Sepharose type or of the protein A-Sepharose type. The fractions containing gliotoxic activity, that is to say a fraction eluted at about 0.2M NaCl and a fraction eluted with D-PBS, respectively, are then used for FPLC chromatography on a Con A-Sepharose type column. Under these conditions, the fractions eluted from the Con A-Sepharose column, either with D-PBS containing up to 500 mM NaCl or thereafter with 200 mM D-glucopyrano-side which displays a competitive affinity for Con A, did not display any gliotoxic activity. The gliotoxic activity present in the original sample was to be found concentrated in the fraction eluted, after the two elutions mentioned above, with 50 mM glycine-HCl buffer, pH 3.0 with 1 mM $Ca^{++}$ and 1 mM $Mn^{++}$. This fraction corresponds to molecules having a high affinity for Con A, which corresponds in general to strongly glycosylated molecules. Analysis of this fraction in one-dimensional SDS-PAGE reveals that the gliotoxic activity is to be found associated with two protein bands of 17 KD and 21 KD, respectively.

An example of analysis on one-dimensional SDS-PAGE gel of a purification using an FPLC column of the DEAE-Sepharose Con A-Sepharose type is presented in FIG. 11. In this example, 27 ml of supernatant containing 100 mg of proteins, from a culture of monocyte/macrophage from a patient suffering from MS, were passed through a DEAE-Sepharose column. [sic] and the eluate obtained with an ionic strength of between 0.12 and 0.20M NaCl was collected in a volume of 10 ml containing 32 mg of proteins. This fraction was then passed through a Con A-Sepharose type column. A first elution was carried out with 500 mm D-PBS, a second elution was carried out with D-PBS buffer containing 200 mM D-glucopyranoside, and a third elution was carried out with 50 mM glycine-HCl buffer, pH 3.0 with 1 mM $Ca^{++}$ and 1 mM $Mn^{++}$, and an eluate of 6.4 ml containing 0.17 mg of proteins was collected.

After this series of purifications in which the gliotoxicity of all the intermediate samples was assayed, 79% of the gliotoxicity of the original supernatant was to be found in the fraction eluted in glycine buffer, pH 3 from the Con A-Sepharose column, with a protein purification yield of 465 times.

On an SDS gel containing 10% of acrylamide, samples from each step were applied successively to parallel wells, corresponding to an amount of protein of 2.2 mg for the third fraction eluted on Con A-Sepharose. It should be noted that still better yields can be obtained for the same steps with CSF from patients suffering from MS.

Furthermore, starting from the third fraction eluted on Con A-Sepharose, a preparative SDS-PAGE electrophoresis was performed in parallel, and different bands were cut out from the unstained gel at the distance corresponding to all the protein bands stained with Coomassie blue in a reference well, as well as from a few regions without protein. To analyze the gliotoxicity of each band thus cut out, the pieces of gel were crushed and homogenized in D-PBS containing 0.2% of SDS, incubated at 37° C. for 30 minutes and then centrifuged at 100,000 g for 6 minutes. The operation is repeated twice, and the supernatants of the two centrifugations are mixed and passed through a DEAE-Sepharose column. The eluate obtained by elution with D-PBS 200 mM NaCl buffer is collected and used for the gliotoxicity tests. Under these conditions, the SDS is retained on the column and the eluate is physiologically compatible with the cell cultures. In these electrophoresis gel extracts, significant gliotoxic activity was to be found only in the bands cut out in the molecular weight regions of approximately 17 KD and 21 KD. in order to verify the protein profile of these two extracts, they were applied to the analytical gel in parallel with the above chromatography fractions. In FIG. 11 presenting the results of the visualization of the proteins which migrated after electrophoresis, starting from the left, the first column shows a series of standard proteins of known molecular weights which are indicated on the left, the second column under "S" shows the starting supernatant, the third column under "T" shows the fraction eluted at between 0.12 and 0.2M NaCl on DEAE-Sepharose, and the fourth, fifth and sixth columns under "II" show the three successive elutions performed on a Con A-Sepharose column and are headed by the serial numbers 1, 2 and 3, respectively, in the order of the above description. The last two columns correspond to the two gliotoxic bands separated and extracted from a preparative SDS-PAGE gel.

From these results it emerges that, as in the analysis performed on MS biological fluids on a Superose 12 column and in one-dimensional SDS-PAGE starting from eluates of filters used for the in vivo filtration of MS CSF, the gliotoxic activity is to be found associated with proteins of apparent molecular weight of approximately 17 KD and 21 KD, with a markedly lower concentration for the 21 KD molecule. However, and contrary to the observations made previously, nongliotoxic control samples passed through a Con A-Sepharose column under the same conditions displayed these bands at 17 KD and 21 KD on SDS-PAGE gel in the fraction eluted in glycine-HCl buffer. Evaluation of the gliotoxic activity of these control samples under the conditions described above does not, however, reveal any significant cytotoxic effect at any step of purification, nor does it do so in the protein bands at approximately 17 KD and approximately 21 KD. Furthermore, "blank" elution of a Con A-Sepharose column with the abovementioned pH 3 glycine-HCl buffer enables the same nongliotoxic bands to be visualized. The possibility of a detachment of protein subunits or fragments of Con A from the chromatography support by the pH 3 glycine buffer was verified. However, in order to verify the reality of a comigration of a novel molecule bearing gliotoxic activity occurring in the bands of approximately 17 and 21 KD originating from MS samples eluted on Con A-Sepharose under the abovementioned conditions, the inventors carried out a digestion, under appropriate conditions, with proteinase K of the fraction originating from a gliotoxic sample and of a nongliotoxic control sample eluted under the same conditions on Con A-Sepharose with the glycine-HCl buffer. The two digestion products were then eluted in parallel on a Superose 12 FPLC column under the conditions mentioned above. These analyses enabled it to be demonstrated that, in the eluate originating from the "MS" sample, an undigested protein peak associated with gliotoxic activity and free from protease activity was always present, whereas all the protein material was degraded in the fractions originating from nongliotoxic control samples previously containing 17- and 21-KD proteins.

An example of this analysis is presented in FIGS. 12 and 13. In this example, a mixture of MS monocyte/macrophage supernatants displaying significant gliotoxic activity and containing 3 g of proteins and an equivalent sample originating from a control culture without significant gliotoxic activity were passed in parallel through a DEAE-Sepharose FPLC column, the fractions eluted at between 0.12 and 0.2M NaCl recovered and the equivalent of 2 mg of proteins for each sample passed through a Con A-Sepharose FPLC column. The fractions eluted in 50 mM glycine-HCl buffer, pH 3 with 1 mM $Ca^{++}$ and 1 mM $Mn^{++}$ were first redissolved in an appropriate buffer. To this end, the samples were lyophilized, resuspended in 2.5 ml of sterile distilled water, applied to an NAP-25 (Pharmacia) type chromatography column previously washed in 10 volumes of 20 mM Tris-HCl buffer, pH 8.0, 1 mM $Ca^{++}$, 0.1% SDS, then eluted with the same buffer and used as they were for incubation with proteinase K. The enzyme used is immobilized (Proteinase K-Acrylic beads, Sigma ref. P0803) and used in a ratio of 20 mU/50–100 µg of protein in 20 mM Tris-HCl buffer, pH 8.0 with 1 mM $Ca^{++}$ and 0.1% SDS. The samples to be digested were incubated for at least 16 hours at 37° C. The supernatants recovered after centrifugation and sedimentation of the beads coupled to proteinase K were then passed through a Superose 12 FPLC column under the conditions described above, and eluted with 50 mM Tris-HCl buffer, pH 6.8 containing 8M urea in order, in particular, to disassociate any multimeric protein. FIG. 12 shows the elution on Superose 12 of the gliotoxic sample originating from MS after treatment with proteinase K. FIG. 13 shows the elution on Superose 12 of the nongliotoxic sample originating from controls not suffering from MS after treatment with proteinase K. The curves in a continuous heavy line show the absorption of the eluate at 280 nm, with an optical density measurement of sensitivity R=0.02, indicating the relative protein concentration. The point of the curve corresponding to the elution of globular proteins of approximately 17 KD is indicated by an arrow. A protein peak of approximately 17 KD is visible only in FIG. 12, and is associated with a gliotoxic activity evaluated at 75% cytotoxicity on a dilution of the sample to ⅒, according to the biological test according to the invention, after 72 h of incubation and quantification of relative cell death by the L/D test. Moreover, in order to detect any trace of contaminant proteinase K, a test of protease activity on azocoll (Sigma ref. A9409) was performed, and did not enable any contaminant protein to be detected at this level. In contrast, a similar absorption peak at 280 nm is detected in both samples below 5 KD and corresponds to the products of degradation of digestible proteins by proteinase K.

The results presented in the example illustrated by FIGS. 12 and 13 show that there is indeed a specific gliotoxic factor present in a novel manner in the biological fluids originating from patients suffering from MS, the factor being associated with one or two polypeptide molecule(s), at least one (or more) 17 KD region(s) of which cannot be digested by proteinase K. However, the mode of purification using Con A-Sepharose columns, while it has enabled a very strong affinity of the gliotoxic factor for concanavalin A to be demonstrated, does not enable appropriate samples to be obtained for a subsequent peptide analysis, as a result of a contamination by components of the concanavalin A originating from the columns under the elution conditions required for eluting said gliotoxic factor. Under these conditions, it seems that a purification protocol successively combining a DEAE-Sepharose column and a Superose 12 column would be best suited to a strategy of purification of molecules bearing the specific gliotoxic activity characterized in the present invention.

An example of analysis of the purification yield with different FPLC columns is presented in Table 3.

In this example, the cytotoxicity is expressed as the amount of protein (mg) needed to have 50% cell death, on the basis of a quantification by a methyltetrazolium colorimetric assay after incubation at 37° C. for 72 h of the test sample diluted to ⅒ in the culture medium. The fractions tested are, for each column type, those which are eluted under the conditions previously described for containing the gliotoxic activity. The yield is calculated according to the following formula:

$$\text{yield } \% = \frac{\text{total proteins } (bp)/\text{cytotoxicity } (bp)}{\text{total proteins } (ap)/\text{cytotoxicity } (ap)} \times 100$$

bp: before purification; ap: after purification.

In this example, it is apparent that protein A-Sepaharose [sic] columns could also be used advisedly, prior to another method of separation excluding Con A-Sepharose columns, in a strategy of purification of the gliotoxic factor.

Lastly, after studying different techniques of purification and preparation of molecular fractions associated with the gliotoxic activity demonstrated in the biological fluids originating from patients suffering from MS, the inventors verified in the study governing the present invention that the purification, even partial, of molecules constituting the molecular basis of the gliotoxic activity affords a dose-response effect which is even more clearly definable than on the crude fluids previously tested, this being done, in particular, in order to verify the biopharmacological reality of the purification of said gliotoxic factor.

The two examples which follow illustrate the reality of a purification of a biopharmacological activity in parallel with the molecular purification performed.

In the example illustrated by attached FIG. No. 14, for which the curves have been plotted from the data presented in the attached Table No. 4, a series of dilutions was made in PBS buffer with a culture supernatant of monocyte/macrophage from a patient suffering from MS (MS 1) , and said dilutions were incubated for 72 hours with a final dilution ranging from 1/20 to 1/5000 in the culture medium of wells comprising a monolayer of astrocytic cells originating from the astrocyte line described above. A fraction of the same MS monocyte culture supernatant, obtained after purification of the gliotoxic fraction by passage through a Con A-Sepharose column, was diluted and incubated in parallel according to the same protocol. The astrocytic cells were incubated, immediately before the introduction of the gliotoxic dilutions, with chromium-51, and washed in order to remove radioactive isotopes not incorporated into the living cells. After 72 hours of incubation with the two series of diluted samples, the radioactivity released into the supernatant is measured with a gamma counter and compared with that measured in the cells remaining in culture at the bottom of the wells. The percentage cytotoxicity, as explained above, represents the proportion of radioactivity released into the supernatant by the dead cells. It may thus be seen in FIG. 14 that there is a dose-response effect marked by a gradual decrease in the cytotoxicity measured as a function of the increasing dilutions of the sample. It should, however, be noted that the slope of the curve is markedly increased, over the same dilution intervals, with the purified factor. This confirms the reality of the purification and of the molecular concentration of the factor associated with the biological activity measured by our test of gliotoxicity.

In the example illustrated by attached FIG. 15, for which the curves were plotted from the data presented in attached Table 5, a series of dilutions was made in PBS buffer with a culture supernatant of monocyte/macrophage from a patient suffering from MS (MS 1), and said dilutions were incubated for 72 hours with a final dilution ranging from 1/20 to 1/5000 in the culture medium of wells comprising a monolayer of astrocytic cells originating from the astrocyte line described above. A fraction of the same MS monocyte culture supernatant, obtained after purification of the gliotoxic fraction by passage through a Con A-Sepharose column, was diluted and incubated in parallel according to the same protocol. After 72 hours of incubation with the two series of diluted samples, cells remaining viable in the culture wells are detected by the methyltetrazolium (MTT) test described above, and the colored product generated by the functional mitochondrial enzymes of these cells is assayed by measuring the optical density of the supernatant at between 570 and 630 nm. The optical density, as explained above, represents the amount of living cells remaining in each well previously inoculated with the same number of cells maintained in a confluent monolayer at the bottom of the culture well in a survival medium. It may thus be seen in FIG. 15 that there is indeed a dose-response effect marked by a gradual increase in cell survival measured as a function of the increasing dilutions of the sample. It should, however, be noted that the slope of the curve is markedly increased, over the same dilution intervals, with the purified factor. This further confirms, by this technique of quantification of living cells, the reality of the purification and of the molecular concentration of the factor associated with the biological activity measured by our test of gliotoxicity.

In the last two examples illustrated by FIGS. 14 and 15, two assay techniques measuring opposite parameters, such as cell survival and relative cell mortality, achieve entirely concordant results and, while enabling the reality of a purification of the gliotoxic activity detected at the same time as gliotoxic factor to be demonstrated, show clearly the discriminatory power and the reliability of the biological test forming, together with the gliotoxic factor characterized by the author's investigations, the subject of the present invention.

Thus, on the basis of the discovery of a cytotoxic activity capable of being demonstrated in vivo in individuals suffering from MS and preferentially targeting the glial cells, a method for detecting and quantifying the cytotoxic, and more especially gliotoxic, activity associated with this factor has been invented, developed and validated under different conditions of use. Furthermore, said method has made it possible to study and characterize the molecular basis of this gliotoxic activity, in the form of protein fractions having two apparent molecular weights of approximately 17 KD and approximately 21 KD, in biological fluids originating, in particular, from patients suffering from MS. The fact that there is a portion which cannot be digested by proteinase K under non-denaturing conditions which is to be found associated with the gliotoxic activity at 17 KD by elution on a Superose 12 FPLC column possibly suggests that an additional peptide which can be digested (propeptide for example) differentiates the 21-KD form from that of 17 K/D. These two factors, apparently of the protein type, of approximately 17 and approximately 21 KD are probably globular, without disulfide bridges connecting independent peptide chains, somewhat hydrophilic, negatively charged at neutral pH and apparently glycosylated despite the fact that incubation in the presence of N-glycosidase F and neuraminidase does not abolish their gliotoxic activity. Furthermore, they display a very high affinity for at least one lectin, concanavalin A or Con A. These protein factors have a biological activity which withstands incubation at 56° C. for half an hour and which disappears after heating at 100° C. for 15 minutes. This biological activity, like the 17-KD form, withstands the action of proteases such as pronase, trypsin and proteinase K.

The detailed description set forth above has finally enabled a gliotoxic factor possessing the following features, taken independently, to be demonstrated:

it possesses cytotoxic activity with respect to glial cells, this cytotoxic activity with respect to glial cells is associated with at least one globular glycoprotein, its activity is linked to at least two protein fractions, associated or otherwise, having an apparent molecular weight of 17 KD and of 21 KD, respectively, each of these fractions possessing gliotoxic activity, the 17-KD fraction being incapable of digestion by pronase or trypsin or proteinase K, and each of these two fractions displaying a strong affinity for lectins such as concanavalin A, the gliotoxic activity of the factor present in a sample persists after heat treatment of the sample at +56° C. for 30 minutes, or after freezing the sample at −80° C. followed by thawing to +37° C., the factor is water-soluble and nonparticulate, the gliotoxic activity of the factor present in a sample persists after treatment of the sample with trypsin or pronase or proteinase K, or a mixture of N-glycosidase F and neuraminidase, under nondenaturing conditions, the factor characterized by one-dimensional SDS-polyacrylamide gel electrophoresis can display two bands, of 17 KD and 21 KD, the gliotoxic factor is retained with a strong affinity on lectin supports, the factor is eluted at pH 7.5 in buffered 100 mM NaCl on DEAE resin, it is not retained by protein A coupled to a support, and can hence be differentiated from IgG, it is to be found in MS monocyte/macrophage culture supernatants and MS CSF and sera, it causes a cytotoxic effect which can be quantified on astrocytic cells in culture and can be characterized by an early effect of disorganization of the network of intermediate filaments, usually followed by cell death.

TABLE 1

EXAMPLE OF APPLICATION OF THE BIOLOGICAL TEST FOR GLIOTOXICITY
Filtration of cerebrospinal fluids from patients suffering from MS with PALL filters

| Patient No. | clinical stage | Percentage of dead cells (L/D test) Before filtration | After filtration | Significance (t-test) |
|---|---|---|---|---|
| 1 | Exacerbation | 14.4 ± 1.7 | 1.4 ± 1.7 | $2.49^{-10}$ |
| 2 | Exacerbation | 35.6 ± 4.55 | 9.7 ± 3.6 | $1.38^{-11}$ |
| 3 | Exacerbation | 20.3 ± 3.59 | 3.2 ± 2.2 | $1.93^{-6}$ |
| 4 | Exacerbation | 29.9 ± 3.28 | 9.7 ± 2.0 | $4.13^{-9}$ |
| 5 | Exacerbation | 45.0 ± 3.46 | 4.2 ± 2.7 | $4.16^{-9}$ |
| 6 | Chronic | 20.8 ± 4.13 | 19.6 ± 2.41 | $5.15^{-1}$ NS |
| 7 | Chronic | 15.5 ± 2.55 | 0.1 ± 0.32 | $9.62^{-9}$ |
| 8 | Probable Clin. | 24.1 ± 3.67 | 0.6 ± 0.84 | $5.55^{-9}$ |
| 9 | Exacerbation | 30.4 ± 4.97 | 4.1 ± 2.38 | $1.46^{-8}$ |
| 10 | Chronic | 24.3 ± 2.31 | 0.6 ± 0.7 | $3.87^{-9}$ |
| 11 | Chronic | 16.0 ± 2.49 | 3.3 ± 2.91 | $9.00^{-9}$ |
| 12 | Exacerbation | 34.9 ± 3.75 | 0.3 ± 0.68 | $4.20^{-9}$ |
| 13 | Exacerbation | 10.5 ± 2.55 | 0 | $3.86^{-7}$ |
| 14 | Exacerbation | 0.6 ± 0.84 | 0 | $5.10^{-2}$ NS |
| 15 | Chronic | 19.7 ± 2.21 | 0.4 ± 0.97 | $3.40^{-8}$ |
| 16 | Chronic stable | 34.5 ± 1.72 | 4.8 ± 2.1 | $3.72^{-9}$ |
| 17 | Chronic | 23.7 ± 2.44 | 0 | $4.66^{-5}$ |
| 18 | Exacerbation | 37.9 ± 1.88 | 2.77 ± 1.55 | $3.98^{-8}$ |
| 19 | Exacerbation | 33.7 ± 2.76 | 1.34 ± 1.98 | $8.76^{-6}$ |
| 20 | Exacerbation | 29.5 ± 2.98 | 2.76 ± 2.21 | $7.45^{-5}$ |
| 21 | Chronic | 24.8 ± 3.76 | 3.21 ± 1.55 | $2.66^{-7}$ |
| 22 | Chronic | 24.9 ± 2.88 | 2.54 ± 2.12 | $3.11^{-8}$ |

*Mean of the cell sin 5 microscopic examination fields chosen at random in 2 duplicate wells. Control cultures show a cell death whose frequency is nonsignificant
+Student's "t"-test.
NS = nonsignificant

TABLE 2

CYTOTOXICITY OF THE CSF FROM PATIENTS SUFFERING FROM MS OR OTHER NEUROLOGICAL DISEASE, DETECTED USING THE BIOLOGICAL TEST ON A LINE OF IMMORTALIZED ASTROCYTES AND QUANTIFIED BY THE MTT COLORIMETRIC METHOD

| PATIENT No. | | CYTOTOXICITY (% dead cells) |
|---|---|---|
| MS | MODE OF PROGRESSION | |
| 1 | Remitting in exacerbation | 48.8 ± 4.5 |
| 2 | Remitting in exacerbation | 54.6 ± 3.9 |
| 3 | Remitting in exacerbation | 44.0 ± 6.5 |
| 4 | Remitting in exacerbation | 39.8 ± 3.8 |
| 5 | Remitting in exacerbation | 52.5 ± 2.9 |
| 6 | Remitting in exacerbation | 68.5 ± 7.7 |
| 13 | Chronic | 7.2 ± 2.2 |
| 14 | Chronic | 8.2 ± 1.9 |
| 15 | Chronic | 4.1 ± 3.0 |
| 16 | Chronic | 0 |
| 17 | Chronic | 5.4 ± 1.7 |
| 18 | Chronic | 6.8 ± 0.8 |
| NPH | (NON-MS CONTROLS) | |
| 19 | | 0 |
| 20 | | 0 |
| 21 | | 0 |
| 22 | | 0 |
| 23 | | 0 |
| 24 | | 0 |

CSF: Cerebrospinal fluid; MTT: Methyltetrazolium; MS: Multiple sclerosis; NPH: Normal pressure hydrocephalus.

Cytotoxicity was measured with the colorimetric technique using MTT after 96 h incubation. CSF samples were diluted to 1:20 in the culture medium used for the immortalized astrocytes.

Each result represents the mean of two separate experiments each representing a series of 5 independent wells, that is to say, finally, a mean of 10 values per CSF tested.

The CSF samples originated from patients suffering from remitting form of MS one [sic] been drawn at the time of clinical exacerbations.

The difference in the mean cytotoxicity values in the two subpopulations of MS, remitting versus chronic, is statistically significant (p <0.0001, Mann-Withney [sic] U test), the difference between the results for MS CSF and that of controls suffering from NPH is itself statistically significant (<0.0001, Mann-Withney [sic] U test).

TABLE 3

EXAMPLE OF PURIFICATION YIELD OF THE GLIOTOXIC FACTOR FROM CULTURE SUPERNATANTS OF MONOCYTES FROM MS PATIENTS

| supernatant | |
|---|---|
| volume (ml) | 10.00 |
| proteins (mg) | 42.00 |
| purification | 1.0 |
| cytotoxicity (mg) | 1.2 |
| yield (%) | 100% |
| protein A-Sepharose | |
| volume (ml) | 8.00 |
| proteins (mg) | 35.30 |
| purification | 1.1 |
| cytotoxicity (mg) | 1.08 |
| yield (%) | 93% |
| concanavalin A-Sepharose + NAP-25 | |
| volume (ml) | 3.50 |
| proteins (mg) | 0.32 |
| purification | 100 |
| cytotoxicity (mg) | 0.012 |
| yield (%) | 76% |

TABLE 4

DOSE-RESPONSE EFFECT: QUANTIFICATION OF THE GLIOTOXIC ACTIVITY BY THE Cr-51-RELEASE TEST

| SAMPLE | DILUTION | BEFORE PURIFICATION % cytotoxicity (in three measurements) | | | AFTER PURIFICATION % cytotoxicity (in three measurements) | | |
|---|---|---|---|---|---|---|---|
| Culture medium | 1/1 | 7.200 | 10.000 | 7.600 | 11.400 | 8.200 | 7.400 |
| Control patient | 1/20 | 11.400 | 10.800 | 10.200 | 7.100 | 6.600 | 8.200 |
| MS 1 | 1/20 | 47.400 | 42.800 | 39.900 | 94.400 | 90.800 | 92.200 |
| MS 1 | 1/200 | 39.000 | 40.400 | 43.100 | 78.800 | 74.200 | 79.400 |
| MS 1 | 1/1000 | 36.200 | 32.400 | 33.300 | 72.100 | 70.400 | 70.000 |
| MS 1 | 1/5000 | 28.100 | 26.600 | 26.400 | 51.200 | 48.400 | 46.200 |

TABLE 5

DOSE-RESPONSE EFFECT: QUANTIFICATION OF THE GLIOTOXIC ACTIVITY BY THE MTT COLORIMETRIC TEST

| SAMPLE | DILUTION | BEFORE PURIFICATION OD 570–630 nm (in three measurements) | | | AFTER PURIFICATION OD 570–630 nm (in three measurements) | | |
|---|---|---|---|---|---|---|---|
| Culture medium | 1/1 | 1.904 | 1.870 | 1.884 | 1.922 | 1.910 | 1.934 |
| Control patient | 1/20 | 1.912 | 1.892 | 1.897 | 1.882 | 1.864 | 1.890 |
| MS 1 | 1/20 | 1.604 | 1.572 | 1.608 | 0.948 | 0.990 | 0.960 |
| MS 1 | 1/200 | 1.812 | 1.794 | 1.800 | 1.310 | 1.302 | 1.322 |
| MS 1 | 1/1000 | 1.890 | 1.914 | 1.888 | 1.760 | 1.784 | 1.762 |
| MS 1 | 1/5000 | 1.902 | 1.896 | 1.890 | 1.890 | 1.824 | 1.818 |

BIBLIOGRAPHY (1) Prineas J. W., The neuropathology of multiple sclerosis in "Handbook of Clinical Neurology: Demyelinating Diseases", volume 3 No. 47, Koetsier J. C. editor, 213–257, Elsevier, Amsterdam 1985.

(2) Prineas J. W., Barnard R. O., Kwon E. E., Sharer L. R. and Cho E. S., Multiple sclerosis: remyelination of nascent lesions. Ann. Neurol., 1993; 33, 137–151.

(3) Boyle E. A. and McGeer P. L., Cellular immune response in multiple sclerosis plaques. American Journal of Pathology, 1993; 137, 575–584.

(4) Charcot J. M., Histologie de la sclérose en plaques [Histology of multiple sclerosis], Gaz. Hop. (Paris), 1868; 41, 554–566.

(5) Hauw J. J. and Escourolle R., Aspects anatomopathologiques de la sclérose en plaques [Anatomopathological aspects of multiple sclerosis], in "La sclérose en plaques" [Multiple sclerosis], Rascol A., Bés A. and Guiraud-Chaumeil B. 9–47. Masson, Paris, 1980.

(6) Poirier J., Fleury J., and Ghérardi R., La barrière hémato-encéphalique, Données morphologiques [The blood-brain barrier, Morphological data], La Revue de Médecine Interne, 1983; 4, 131–144.

(7) Netsky M. G., and Shuangshoti S., The choroid plexus in health and disease, University Press of Virginia, 1975.

(8) Gonzales-Scarano F., Grossman R. I., Galetta S. Atlas S. W. and Silberberg D. H., Multiple slerosis [sic] disease activity correlates with gadolinium enhancement magnetic resonance imaging. Ann. Neurol., 1987; 21, 300–306.

(9) Rapport S. I., Blood-brain barrier in physiology and medicine, Raven Press. 1976.

(10) Kent T. A. and McKendall R. R., Cerebral blood flow, cerebral metabolism and blood-brain barrier, In, McKendall R. R. Ed., Handbook of Clinical Neurology, Vol. 12, No. 56: Viral disease, Elsevier, Amsterdam, 1989.

(11) Prineas J. W. and Wright R. G., Macrophages, lymphocytes, and plasma cells in the perivascular compartment in chronic multiple sclerosis, Laboratory Investigation, 1978; 38, 409–421.

(12) Bergamini L., and Durell L., Multiple sclerosis, I, The immune pathogenetic hypothesis, Riv. Neurol., 1989; 59, 176–90.

(13) Calder V, Owen S, Watson C., Feldmann M, and Davidson A., MS: a localized immune disease of central nervous system, Immunol Today, 1989; 10, 99–103.

(14) Jervis G. A., and Koprowski H., Chronic experimental allergic encephalomyelitis, J. Neuropathol. Exp. Neurol., 1948; 7, 309–320.

(15) Prineas J W., Pathology of early lesion in multiple sclerosis, Human pathology, 1975; 6, 23–7.

(16) Escourolle R., Hauw J. J. and Lyon-Caen O., Principales données morphologiques, approches physiopathologiques et étiologiques de la sclérose en plaques [Principal morphological data, physiopathological and etiological approaches to multiple sclerosis], La Revue du Praticien (Paris), 1980; 30, 2047–2053.

(17) Mc Donald W. I., The mystery of the origin of multiple sclerosis, J. Neurol. Neurosurg. Psych., 1986; 49, 113–123.

(18) Carp R. I., Warner H. B. and Merz G. S., Viral etiology of multiple sclerosis., Prog. Med. Virol., 1978; 24, 158–177.

(19) Marie P., Sclérose en plaques et maladies infectieuses [Multiple sclerosis and infectious diseases], Le progrès médical, 1884; 12, 287–289.

(20) Gay D, Dick G, and Upson G., Multiple sclerosis caused by an oral spirochete?, Lancet; 1986, 2, 815–9.

(21) De Keyser J. Autoimmunity in multiple sclerosis. Neurology, 1988 March, 38, 371–4.

(22) Juntunen J, Kinnunen E, Anti-Poika M, Koskenvuo M. Multiple sclerosis and occupational exposure to chemicals: a co-twin control study of a nationwide series of twins, Br. J. Int. Med., 1989; 417–9.

(23) Ebers G. C., Bulman D., The geographic distribution of MS reflects genetic susceptibility, Neurology, 1986; 36, S1–108.

(24) Haegert D. G., Michaud M., Schwab C., Tansey C., Secary F., Francis G., HLA-DR beta, -DQ alpha and -DQ beta restriction fragment length polymorphisms in multiple sclerosis, J. Neurosci. Res., 1989; 23, 46–54.

(25) Waksman B. H., Mechanisms in Multiple Sclerosis, Nature, 1985; 318, 104–105.

(26) Acha-Orbea H. and Palmer E., Mls - a retrovirus exploits the immune system, Immunology Today 1991; 12, 356–361.

(27) Cole B. C. and Atkin C. L., The mycoplasma arthritidis T-cell mitogen, MAM: a model superantigen, Immunology Today 1991; 12, 271–276.

(28) Rudge P., Does a retrovitally encoded superantigen cause multiple sclerosis?, Journal of Neurology, Neurosurgery and Psychiatry, 1991; 54, 853–855.

(29) Woodland D. L., Happ M. P., Gollob K. J. and Palmer E., An endogenous retrovirus mediating deletion of aβ T cells? Nature (London), 1991; 349, 529–530.

(30) Traugott U., Multiple sclerosis: relevance of class I and class II MHC-expressing cells to lesion development, Journal of Neuroinumunology, 1987; 16, 283–302.

(31) Williams G. T. and Smith C. A., Molecular regulation of apoptosis: genetic controls on cell death, Cell, 1993; 74, 777–779.

(32) Levine B., Huang Q., Isaacs J. T., Reed J. C., Griffin D. E. and Hardwick J. M., Conversion of lytic to persistent alphavirus infection by the bcl-2 cellular oncogene, Nature, 1993; 361, 739–742.

(33) Newell M. K., VanderWall J., Beard K. S. and Freed J. H., Ligation of major histocompatibility complex class II molecules mediates apoptotic cell death in resting B lymphocytes, P.N.A.S., 1993; 90, 10459–10463.

(34) Selmaj. K. W. and Raine C. S., Tumor necrosis factor mediates myelin and oligodendrocyte damage in vitro, Ann. Neurol., 1988; 23, 339–346. ( 35) Barna B. P., Estes M. L., Jacobs B. S., Hudson S. and Ransohoff R. M., Human astrocytes proliferate in response to tumor necrosis factor alpha, J. Neuroimmunol., 1990; 30, 239–243

(36) Robbins D. S., Shirazi Y., Drysdale B. E., Lieberman A., Shin H. S. and Shin M. L., Production of cytotoxic factor for oligodendrocytes by stimulated astrocytes, The journal of Immunology 1987; 139, 2593–2597.

(37) Beck J., Rondot P., Catinot L., Falcoff E., Kirchner J. and Wietzerbin J., Increased production of interferon gamma and tumor necrosis factor precedes clinical manifestation in multiple sclerosis: do cytokine [sic] trigger off exacerbations?, Acta Neurol. Scand., 1988; 78, 318–323.

(38) Kaufmann S. H. E., Heat Shock Proteins and Immune Response, Current Topics in Microbiology and Immunology, vol. 167, Springer-Verlag, Berlin, 1991.

(39) Wienfield J. B., and Jarjour W. N., Stress proteins, autoimmunity, and autoimmune disease, in Heat Shock Proteins and Immune Response, Kaufmann S. H. E., Current Topics in Microbiology and Immunology, vol. 167, 161–189, Springer-Verlag, Berlin, 1991.

(40) Brocke S., Gaur A., Piercy C., Gautam A., Gijbels K., Fathman C. G. and Steinman L., Induction of relapsing paralysis in experimental autoimmune encephalomyelitis by bacterial superantigen, Nature, 1993; 365, 642–644.

(41) Birnbaum G., Kotilinek L. and Albrecht L., Spinal fluid lymphocytes from a subgroup of multiple sclerosis patients respond to mycobacterial antigens, Ann. Neurol. 1993; 34, 18–24.

(42) Ransohoff R. M. and Rudick R. A., Heat-shock proteins and autoimmunity: implications for multiple sclerosis, Annals of Neurology, 1993; 34, 5–7.

(43) Perron H. Geny C., Laurent A., et al., Leptomeningeal cell line from multiple sclerosis with reverse transcriptase activity and viral particles, Res. Virol., 1989; 140, 551–561.

(44) Perron H., Geny C., Gratacap B., Laurent A., Mouriquand C., Pellat J., Perret J., and Seigneurin J. M., Isolation of an unknown retrovirus from CSF, blood and brain from patients with multiple sclerosis, in "Current concepts in multiple sclerosis", Wiethölter et al., pp. 111–116. Elsevier, Amsterdam, 1991.

(45) Perron H., Lalande B., Gratacap B., Laurent A., Genoulaz O., Geny C., Mallaret M., Schuller E., Stoebner P., and Seigneurin J. M., Isolation of retrovirus from patients with multiple sclerosis, Lancet, 1991; 337, 862–863.

(46) Dalgleish A. G., Fazakerley J. K. and Webb H. E., Do human T-lymphotropic viruses (HTLVs) and other enveloped viruses induce autoimmunity in multiple sclerosis?, Neuropath. Appl. Neurobiol., 1987; 13, 241–250.

(47) Birnbaum G., Kotilinek L. and Albrecht L., Spinal fluid lymphocytes from a subgroup of multiple sclerosis patients respond to mycobacterial antigens, Ann. Neurol., 1993; 34, 18–24.

(48) Davison A. N. and Sabri M. L, Biosynthesis of Myelin and Neurotoxic Factors in the Serum of Multiple Sclerosis Patients, Advances in Experimental Medicine, vol. 100, 1978, New York, U.S., 19–25.

(49) Poser C. M. et al., New diagnostic criteria for multiple sclerosis: guidelines for research protocols, in "The diagnosis of multiple sclerosis", Poser C. M., Paty D. W., ScheirLberg L., MacDonald W. I., Ebers G. C. pp. 225–229, 1984, Thieme Stratton Inc., New York.

(50) Galiana E., Borde I., Marin P., Rassoulzadegan M., Cuzin F., Gros F., Rouget P. and Evrard C., Establishment of permanent astroglial cell lines, able to differentiate in vitro, from transgenic mice carrying the polyoma virus large-T gene: an alternative approach to brain cell immortalization, Journal of Neuroscience Research, 1990; 26; 269–277.

(51) Mosmann T., Rapid colorimetric assay of cellular growth and survival: application to proliferation and cytotoxicity assays, J. Immunol. Meth., 1983; 65, 55–63.

(52) Wollinsky K. H., Hülser P. J., Mauch E., Mehrkens H. H. and Kornhuber H. H., Liquorpherese bei 10 Patienten mit Multipier sklerose [Fluid pheresis in 10 patients with multiple sclerosis] in verhandlungen [sic] der Deutschen Gesellschaft für Neurologie, Grundmann M et al., vol 7 (1992) Saarbrücken.

(53) Bradford M. M., A rapid sensitive method for the quantitation of microgramquantities of protein utilizing the principle of protein-dye binding, Anal. Biochem., 1976; 72, 248–254.

(54) Silberberg D. et al., Tissue culture demyelination by normal human serum, Annals of Neurology, 1984: 15, 575–580.

What is claimed:

1. A method for analyzing an activity of a pathology associated with a gliotoxic factor having toxic activity with respect to macroglial cells, said method comprising:

obtaining a biological sample;

incubating said sample with said macroglial cells; and assaying said gliotoxic factor in said biological sample by detecting apoptosis in said macroglial cells.

2. The method according to claim 1, wherein the pathology is multiple sclerosis.

3. A method for pretreating a biological sample comprising a gliotoxic factor having toxic activity with respect to astrocytic cells, said method comprising contacting said sample with at least one member selected from the group consisting of protein A, an ion exchange resin and a lectin.

4. The method according to claim 3, wherein the lectin is concanavalin A.

5. A method for assaying, in a biological sample, the toxic activity of a gliotoxic factor having toxic activity with respect to astrocytic cells, said method comprising:

incubating said biological sample in a culture medium containing astrocytes, culturing said astrocytes, and assaying at least one population selected from the group consisting of dead astrocytes and living astrocytes.

6. The method according to claim 5, further comprising:

assaying the dead astrocytes with a first colorimetric assay method employing calcein-AM; and assaying the living astrocytes by a second colorimetric assay method employing ethidium homodimer.

7. The method according to claim 5, further comprising assaying the living astrocytes with a colorimetric assay method employing methyltetrazolium bromide.

8. The method according to claim 5, further comprising assaying the dead astrocytes with a radioactive assay method employing $^{51}$Cr.

9. The method according to claim 5, wherein the culture medium comprises immortalized astrocytes.

10. A method for assaying, in a biological sample, the toxic activity of a gliotoxic factor having toxic activity with respect to astrocytic cells, said method comprising:

incubating said sample in a culture medium comprising astrocytes, culturing said astrocytes, and performing at least one assay from the group consisting of assaying fragmentation of DNA of the astrocytes, assaying cytomorphological disorganization of a network of intermediate filaments, and assaying degradation of proteins of said intermediate filaments.

11. The method according to claim 10, wherein said astrocytes are immortalized.

12. A method for assaying, in a biological sample, a gliotoxic factor having toxic activity with respect to astrocytic cells, said method comprising:

obtaining the biological sample to be assayed;

contacting the biological sample with a composition comprising a ligand that binds to the gliotoxic factor; and qualitatively or quantitatively assaying an amount of the ligand bound to the gliotoxic factor to qualitatively or quantitatively assay an amount of the gliotoxic factor in said sample.

13. The method according to claim 12, wherein the ligand is a lectin.

14. The method according to claim 13, wherein the lectin is concanavalin A.

15. The method according to claim 12, wherein the ligand is an antibody specific to the gliotoxic factor.

16. The method according to claim 12, wherein the ligand is bound to a solid support.

17. The method according to claim 16, wherein the solid support is a filter.

18. A method for assaying, in a biological sample, a gliotoxic factor having toxic activity with respect to astrocytic cells, said method comprising:

loading the biological sample onto a solid support to which a first ligand is bound;

binding the gliotoxic factor in the biological sample to the first ligand;

washing unbound portions of the biological sample off of the solid support;

loading a composition comprising a second ligand onto the solid support;

binding the second ligand to the gliotoxic factor bound to the first ligand bound to the solid support;

washing unbound portions of the composition off of the solid support; and qualitatively or quantitatively assaying an amount of the second ligand bound to the gliotoxic factor bound to the first ligand bound to the solid support to qualitatively or quantitatively assay an amount of the gliotoxic factor in said sample.

19. The method according to claim 18, wherein the second ligand comprises a marker.

20. The method according to claim 18, further comprising binding a marker to the second ligand bound to the gliotoxic factor bound to the first ligand bound to the solid support.

* * * * *